United States Patent
Hayashi

(10) Patent No.: US 8,716,500 B2
(45) Date of Patent: May 6, 2014

(54) METHOD FOR PRODUCING FIVE-MEMBERED RING-CONTAINING COMPOUND

(75) Inventor: Yujiro Hayashi, Tokyo (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 14/113,611

(22) PCT Filed: Apr. 27, 2012

(86) PCT No.: PCT/JP2012/061393
§ 371 (c)(1),
(2), (4) Date: Oct. 24, 2013

(87) PCT Pub. No.: WO2012/147925
PCT Pub. Date: Nov. 1, 2012

(65) Prior Publication Data
US 2014/0051874 A1    Feb. 20, 2014

(30) Foreign Application Priority Data

Apr. 28, 2011   (JP) .................................. 2011-100636

(51) Int. Cl.
*C07D 307/02*    (2006.01)

(52) U.S. Cl.
USPC ........................................................ 549/491

(58) Field of Classification Search
USPC ........................................................ 549/491
See application file for complete search history.

(56) References Cited

FOREIGN PATENT DOCUMENTS

JP    2009-091257 A    4/2009

OTHER PUBLICATIONS

B. Tan et al.; "Facile Domino Access to Chiral Bicyclo[3.2.1]octanes and Discovery of a New Catalytic Activation Mode"; Organic Letters; American Chemical Society; May 14, 2010; vol. 12, No. 12, pp. 2682-2685.

Y. Hayashi et al.; "Diphenylprolinol Silyl Ether as a Catalyst in an Enantioselective, Catalytic, Tandem Michael/Henry Reaction for the Control of Four Stereocenters"; Communications; Angew. Chem. Int. Ed.; 2007; vol. 46, No. 26, pp. 4922-4925.
International Search Report for PCT/JP2012/061393, submitted Oct. 24, 2013.

*Primary Examiner* — Kristin Vajda
(74) *Attorney, Agent, or Firm* — Sughrue Mion, PLLC

(57) ABSTRACT

The present invention provides a method that allows production of stereospecific and asymmetrical five-membered ring-containing compounds serving as synthetic intermediates for formation of five-membered rings of prostaglandins and the like, with high yield and excellent stereoselectivity in terms of diastereoselectivity and enantioselectivity in a short process without requiring troublesome procedures such as optical resolution. The method for producing a five-membered ring-containing compound includes a cyclization step of condensing and cyclizing an α,β-unsaturated nitro compound represented by the following chemical formula (I) with a 1,4-butanedione compound, in the presence of a catalyst formed by a compound having a pyrrolidine ring and an optically active α-carbon relative to the nitrogen on the ring, in a water-insoluble organic solvent and/or a non-oxygen atom-containing water-soluble organic solvent so as to produce the five-membered ring-containing compound represented by the following chemical formula (II).

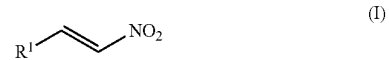

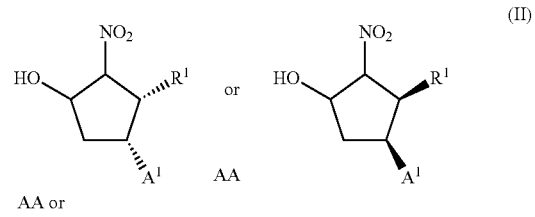

16 Claims, No Drawings

METHOD FOR PRODUCING FIVE-MEMBERED RING-CONTAINING COMPOUND

TECHNICAL FIELD

The present invention relates to a method for stereoselectively producing an asymmetrical five-membered ring-containing compound which is a synthetic intermediate for five-membered ring-containing physiologically active compounds serving as pharmacologically active components of prostaglandin pharmaceutical formulations and the like.

BACKGROUND ART

PGEs including prostaglandin (hereinafter referred to as PG) $E_1$ and $E_2$ and PGFs including $PGF_{2\alpha}$ are known as metabolites of the arachidonate cascade. For example, $PGE_2$ is known to have cell protection effect, uterine contraction, pain generation effect, promoting peristaltic movement of gastrointestinal tract, arousal effect, gastric secretion inhibition effect, hypotensive effect, diuretic effect and the like.

PGs containing a five-membered ring such as PGEs and PGFs are produced through multiple steps using a so-called Corey lactone as a synthetic intermediate for controlling stereoselectivity at the α side chain group, ω side chain group, hydroxyl group and the like on a five-membered ring, the Corey lactone being a cyclopenta[b]furan-2-one compound which is synthesized from, for example, cyclopentadiene as a starting material through complicated multiple steps including troublesome optical resolution.

These PGs, which are used as pharmacologically active components for pharmaceutical formulations, are required to be produced while controlling undesired potential impurities such as diastereomers and enantiomers.

Therefore, there is a need for producing in good yield an appropriate synthetic intermediate which composes a five-membered ring of PGs in a shorter process than the synthesis process of Corey lactone with excellent stereoselectivity in terms of diastereoselectivity and enantioselectivity.

Meanwhile Non-Patent Literature 1 discloses stereoselective asymmetrical synthesis of bicyclo[3.2.1]octanes by reacting an active methylene of cyclohexanedione carboxylic acid methyl esters with nitroolefins in the presence of quinine alkaloid catalysts by the Michael-Henry reaction to form five-membered rings de novo. This asymmetrical synthesis does not correspond to the production of monocyclic five-membered ring-containing compounds required for production of PGs.

Patent Literature 1 discloses a method for obtaining a product from the Michael reaction of α,β-unsaturated aldehydes and nitroalkanes in the presence of asymmetrical pyrrolidine methanol derivative catalysts. This method does not correspond to the production of cyclic five-membered ring-containing compounds required for production of PGs.

Non-Patent Literature 1: Bin Tan et al., Organic Letters, 2010, vol. 12, p. 2682-2685
Patent Literature 1: Japanese Patent Application Laid-open No. 2009-91257

DISCLOSURE OF THE INVENTION

The present invention is achieved in order to solve the above problem. Namely, an object of the present invention is to provide a method that allows convenient production of stereospecific and asymmetrical five-membered ring-containing compounds serving as synthetic intermediates for formation of five-membered rings of PGs and the like, with a high yield and excellent stereoselectivity in terms of diastereoselectivity and enantioselectivity in a short process without requiring troublesome procedures such as optical resolution. Another object of the present invention is to provide stereospecific and asymmetrical five-membered ring-containing compounds obtained by the method.

The invention according to claim 1 which has been achieved in order to attain the above objects is a method for producing a five-membered ring-containing compound represented by the following chemical formula (II):

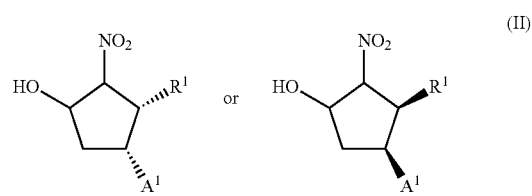

wherein in the formula (II), $R^1$ may contain a substituent and is selected from a hydrocarbon ring group, a heterocyclic group, a hydrocarbon ring-containing alkyl group, a heterocycle-containing alkyl group, an alkyl group, an alkenyl group, an alkynyl group, an alkyl thioether-containing alkyl group, a heterocyclic group-containing alkyl thioether group, a hydrocarbon ring group-containing alkyl ether group and an alkyloxycarbonyl group; $A^1$ is an aldehyde group or a hydroxymethyl group obtained by reduction thereof; and among the configuration symbols,

represents the α-configuration and

represents the β-configuration, the method including a cyclization step of condensing and cyclizing an α,β-unsaturated nitro compound represented by the following chemical formula (I):

wherein in the formula (I), $R^1$ is as described above, with a 1,4-butanedione compound, in the presence of a catalyst formed by a compound having a pyrrolidine ring and an optically active α-carbon relative to the nitrogen on the ring, in a water-insoluble organic solvent and/or a non-oxygen atom-containing water-soluble organic solvent.

The invention according to claim 2 is the method for producing a five-membered ring-containing compound according to claim 1, further including, after the cyclization step, a reduction step of reducing, with a reducing agent, the $A^1$ that is the aldehyde group to the hydroxymethyl group.

The invention according to claim 3 is the method for producing a five-membered ring-containing compound according to claim 1 or 2, wherein the catalyst is a proline derivative represented by the following chemical formula (III):

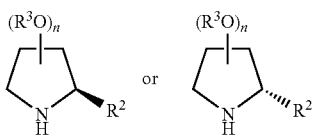

wherein in the formula (III), $R^2$ is a carboxyl group, a tetrazole group or a —$C(R^4)(R^5)OR^6$ group [wherein $R^4$ and $R^5$ respectively and independently may contain a substituent and are selected from a hydrocarbon aromatic ring group, a heteroaromatic ring group and an alkyl group; and $R^6$ is a hydrogen atom, a silyl group or an alkyl group]; $R^3$ represents a protective group; n represents a number of 0 to 1; and configuration symbols are the same as above.

The invention according to claim 4 is the method for producing a five-membered ring-containing compound according to claim 3, wherein the proline derivative represented by the chemical formula (III) corresponds to:

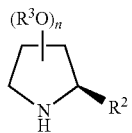

wherein in the formula (IIIa), all symbols are the same as above, and the five-membered ring-containing compound represented by the chemical formula (II) corresponds to:

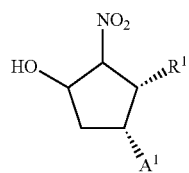

wherein in the formula (IIa), all symbols are the same as above.

The invention according to claim 5 is described in claim 3 and characterized in that the proline derivative represented by the chemical formula (III) corresponds to:

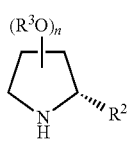

wherein in the formula (IIIb), all symbols are the same as above, and the five-membered ring-containing compound represented by the chemical formula (II) corresponds to:

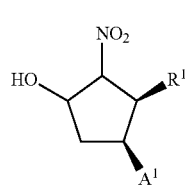

wherein in the formula (IIb), all symbols are the same as above.

The invention according to claim 6 is the method for producing a five-membered ring-containing compound according to any of 1 to 5, wherein the water-insoluble organic solvent is at least one selected from a halogen-containing organic solvent, an aromatic organic solvent, a hydrocarbon organic solvent and an acyclic ether organic solvent, and the non-oxygen atom-containing water-soluble organic solvent is a nitrile-substituted hydrocarbon organic solvent.

The invention according to claim 7 is described in claim 6 and is characterized in that the water-insoluble organic solvent is the halogen-containing organic solvent selected from dichloromethane, dichloroethane and chloroform; the aromatic organic solvent selected from benzene, toluene and xylene; the hydrocarbon organic solvent selected from pentane, hexane and heptane; and/or the acyclic ether organic solvent that is diethyl ether, and the non-oxygen atom-containing water-soluble organic solvent is the nitrile-substituted hydrocarbon organic solvent that is acetonitrile.

The invention according to claim 8 is the method for producing a five-membered ring-containing compound according to any of claims 1 to 7, wherein the cyclization step is performed in the presence of both the catalyst and an acid.

The invention as in claim 9 is the method for producing a five-membered ring-containing compound according to claim 8, wherein the acid has a pKa in water at 25° C. of 4 to 10.

The invention according to claim 10 is the method for producing a five-membered ring-containing compound according to claim 8 or 9, wherein the acid is at least one free acid selected from the group consisting of a fatty acid derivative containing 1 to 3 carbon atoms, an aromatic carboxylic acid derivative, a hydroxyaromatic derivative and a perfluoroalkyl group-containing alcohol.

The invention according to claim 11 is the method for producing a five-membered ring-containing compound according to any of claims 1 to 10, wherein the substituent in $R^1$ of the chemical formula (I) is at least one selected from the group consisting of a linear or branched alkoxy group containing 1 to 4 carbon atoms, an ester group and a halogen atom.

The invention according to claim 12 is the method for producing a five-membered ring-containing compound according to any of claims 1 to 11, wherein the catalyst is (S)-2-(diphenyl((trimethylsilyl)oxy)methyl)pyrrolidine or (R)-2-(diphenyl((trimethylsilyl)oxy)methyl)pyrrolidine.

The invention according to claim 13 is the method for producing a five-membered ring-containing compound according to claim 2, wherein the reducing agent is at least one selected from the group consisting of $NaBH_4$, $NaBH_3CN$, $B_2H_6$, $BH_3.Me_2S$, $LiAlH_4$, $NaB(O_2CCH_3)_3H$ and $LiBH(C_2H_5)_3$.

The invention according to claim 14 which has also been achieved in order to attain the above objects is a five-membered ring-containing compound represented by the following chemical formula (IV):

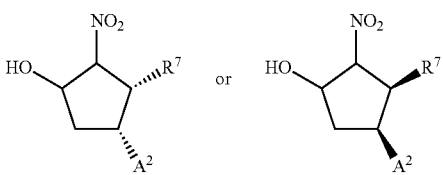

wherein in the formula (IV), $R^7$ may contain a substituent and is selected from a hydrocarbon ring group, a heterocyclic group, a hydrocarbon ring-containing alkyl group, a heterocycle-containing alkyl group, an alkyl group, an alkenyl group, an alkynyl group, an alkyl thioether-containing alkyl group, a heterocyclic group-containing alkyl thioether group, a hydrocarbon ring group-containing alkyl ether group and an alkyloxycarbonyl group;

$A^2$ is an aldehyde group or a hydroxymethyl group; and among the configuration symbols, represents the α-configuration and represents the β-configuration.

The invention according to claim 15 is the five-membered ring-containing compound according to claim 14, wherein in the chemical formula (IV), the $R^7$ may contain a substituent and is selected from a cyclohexyl group, a phenyl group, a naphthyl group, a furyl group, a phenethyl group, a benzyloxy ethyl group and an alkyloxycarbonyl group.

The invention according to claim 16 is the five-membered ring-containing compound according to claim 14 or 15, wherein in the chemical formula (IV), the $R^7$ is any of those represented by the following chemical formula (V):

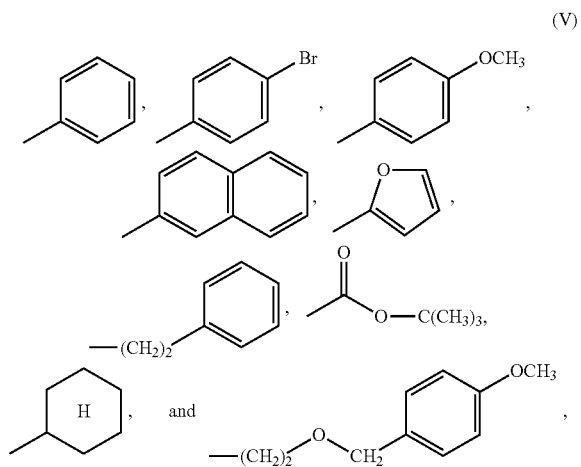

According to the method for producing a five-membered ring-containing compound of the present invention, stereospecific and asymmetrical five-membered ring-containing compounds serving as synthetic intermediates for formation of five-membered rings of PGs can be conveniently produced, with diastereoselectivity and enantioselectivity, from acyclic starting materials in one cyclization step. The five-membered ring-containing compounds obtained by this method are highly stereoselective in terms of diastereoselectivity and enantioselectivity and can be obtained with a high yield.

The method allows direct and stereoselective production of asymmetrical five-membered ring-containing compounds and thus does not require inefficient and troublesome optical resolution which may produce undesired optically active substances. This method further allows asymmetrical synthesis of desired five-membered ring-containing compounds with a preferable yield over a wide range from a laboratory scale of the level between 0.1 millimoles to a few millimoles to a plant scale of the level between a few kg to a ton.

The five-membered ring-containing compound of the present invention is stereospecific and has high optical purity, and thus can be used as a synthetic intermediate for stereoselective production of various five-membered ring-containing physiologically active compounds typified by PGs such as $PGE_1$, $PGE_2$ and $PGF_{2\alpha}$, which are pharmacologically active components of PG pharmaceutical formulations. The five-membered ring-containing compound can derive desired PGs by homologation of the α side chain group or ω side chain group or by subsequent functional modification or conversion.

BEST MODE FOR CARRYING OUT THE INVENTION

The embodiments of the present invention are hereinafter specifically described. However, the scope of the invention is not limited to these embodiments.

The preferable embodiments of the present invention are described by referring to the following chemical reaction formulae (VI) and (VII).

The method for producing a five-membered ring-containing compound of the present invention is the one obtaining the five-membered ring-containing compound through the cyclization step of condensing and then cyclizing, via the Michael-Henry reaction, a 1,4-butanedione compound (2) and an α,β-unsaturated nitro compound (3) in the presence of a catalytic amount of an asymmetrical proline derivative (1) and optionally a catalytic amount of an acid so as to form a five-membered ring in one step and derivatizing to a cyclized five-membered ring-containing compound (7). A different five-membered ring-containing compound (9) may be obtained through the reduction step of reducing, with a reducing agent, the cyclized five-membered ring-containing compound (7) after or without isolation to derive a reduced five-membered ring compound (8). The cyclized five-membered ring-containing compound (7) may be subjected to, after or without isolation, homologation of the aldehyde group by the Horner-Wadsworth-Emmons reaction or the Wittig reaction. These compounds may be appropriately derived to a PG (10).

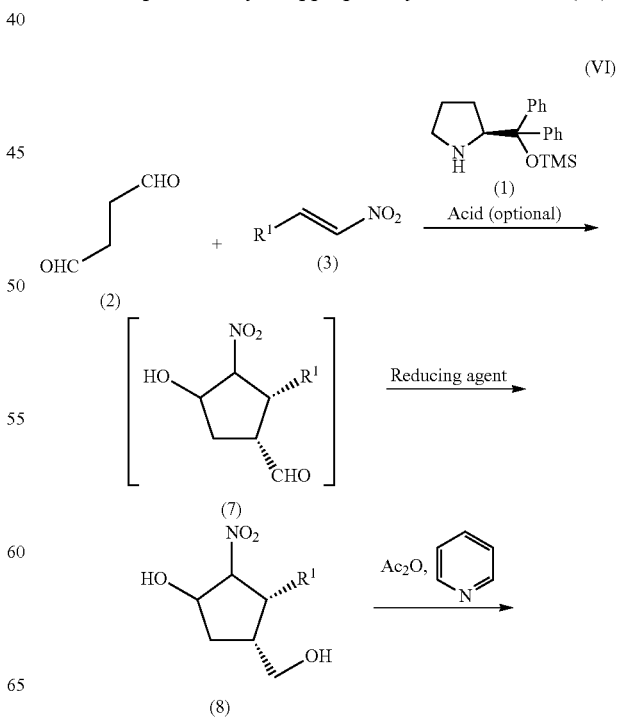

-continued

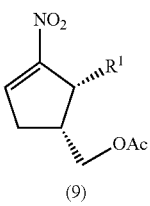

(9)

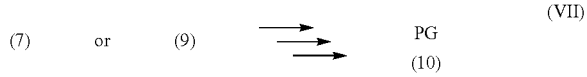

(VII)

In the chemical reaction formula (VI), $R^1$ of the α,β-unsaturated nitro compound (3) may contain a substituent which may specifically be:

a saturated and/or unsaturated and aliphatic or aromatic hydrocarbon ring group containing 3 to 10 carbon atoms, e.g. a phenyl group, a naphthyl group, a cyclopropyl group, a cyclobutyl group, a cyclopentyl group, a cyclohexyl group, a cycloheptyl group, a cyclooctyl group, a cyclononyl group or a cyclodecyl group;

a saturated and/or unsaturated heterocyclic group with a five- to six-membered ring such as a heteroaryl or heteroalicyclic group, e.g. a furyl group, an oxazolyl group, an isoxazolyl group, a thiazolyl group, an isothiazolyl group, an oxadiazolyl group, a pyrrolyl group, a triazolyl group, an imidazolyl group, a pyrazolyl group, a thienyl group, a pyridyl group or a morphonyl group;

a hydrocarbon ring-containing alkyl group which is an alkyl group containing 1 to 4 carbon atoms and the hydrocarbon ring group as described above, e.g. an aralkyl group such as a benzyl group and a phenethyl group or a cycloalkyl-substituted alkyl group;

a heterocycle-containing alkyl group which is an alkyl group containing 1 to 4 carbon atoms and the heterocyclic group as described above, e.g. a pyridylmethyl group, a pyridylethyl group or a thiazolylmethyl group;

a linear, branched and/or cyclic alkyl group containing 1 to 10 carbon atoms, e.g. a methyl group, an ethyl group, a propyl group, a butyl group, a pentyl group, a hexyl group, a heptyl group, an octyl group, a nonyl group, a decyl group, a cyclopropyl group, a cyclobutyl group, a cyclopentyl group, a cyclohexyl group, a cycloheptyl group, a cyclooctyl group, a cyclononyl group or a cyclodecyl group;

a linear, branched and/or cyclic alkenyl group containing 2 to 6 carbon atoms, e.g. a vinyl group, a propenyl group, a butenyl group, a butadienyl group, a pentenyl group, a pentadienyl group, a hexenyl group, a hexadienyl group, a cyclopropenyl group, a cyclobutenyl group, a cyclopentenyl group or a cyclohexenyl group;

a linear, branched and/or cyclic alkynyl group containing 2 to 6 carbon atoms, e.g. an ethynyl group, a propynyl group, a butynyl group, a butadienyl group, a pentynyl group, a pentadiynyl group, a hexynyl group or a hexadiynyl group;

an alkyl thioether-containing alkyl group which is an alkyl group containing 1 to 4 carbon atoms and an alkyl thioether group with 1 to 4 carbon atoms, e.g. an ethylthiomethyl group (—CH$_2$—S—CH$_2$CH$_3$), a propylthioethyl group (—(CH$_2$)$_2$—S—(CH$_2$)$_2$CH$_3$) or a butylthiobutyl group (—(CH$_2$)$_4$—S—(CH$_2$)$_3$CH$_3$);

a heterocycle-containing alkyl thioether group which is the alkyl thioether group as described above containing the heterocyclic group as described above, e.g. a pyridylthioethyl group (—(CH$_2$)$_2$—S-pyridyl group), a pyridylethylthiomethyl group (—CH$_2$—S—(CH$_2$)$_2$-pyridyl group), a thiazolylthioethyl group (—(CH$_2$)$_2$—S-thiazolyl group) or a thiazolylethylthiomethyl group (—CH$_2$—S—(CH$_2$)$_2$-thiazolyl group);

a hydrocarbon ring-containing alkyl ether group which is an alkyl ether group containing 1 to 4 carbon atoms and the hydrocarbon ring group as described above, e.g. a benzyloxyethyl group, a phenethyloxyethyl group or a benzyloxypropyl group; or an alkyloxycarbonyl group containing an alkyloxy of 1 to 4 carbon atoms, e.g. a tert-butoxycarbonyl group, a methoxycarbonyl group, an ethoxylcarbonyl group, a propoxycarbonyl group or an isopropoxycarbonyl group.

The position of the potential substituent on $R^1$ is not particularly limited.

Among these, $R^1$ of the α,β-unsaturated nitro compound (3) is further preferably a phenyl group, a bromophenyl group, a methoxyphenyl group, a naphthyl group, a furyl group, a phenethyl group, a tert-butoxycarbonyl group, a cyclohexyl group or a methoxybenzyloxyethyl group as shown in the chemical formula (V), and particularly preferably a phenyl group, a bromophenyl group, a methoxyphenyl group or a naphthyl group.

In the chemical reaction formula (VI), the 1,4-butanedione compound (2) is exemplified by succinaldehyde; however it may be succinaldehyde containing a substituent. Succinaldehyde (CAS (Chemical Abstracts Service) registry number: 638-37-9) may be the one commercially available or may be produced, or prepared upon use if required, according to the well known method such as the method described in U.S. Pat. No. 2,920,081 (description).

The five-membered ring-containing compound represented by the chemical formula (IV) of the present invention may be obtained by the method for producing a five-membered ring-containing compound of the present invention or by a different method. The five-membered ring-containing compound represented by the chemical formula (IV) has a stereospecific cyclohexane ring of various physiologically active substances typified by PGs such as PGEs and PGFs, and thus can serve as an intermediate for these physiologically active substances.

$R^7$ in the chemical formula (IV) corresponds to $R^1$ in the chemical formula (II). Specifically, $R^7$, as described above, may contain a substituent, is selected from a hydrocarbon ring group, a heterocyclic group, a hydrocarbon ring-containing alkyl group, a heterocycle-containing alkyl group, an alkyl group, an alkenyl group, an alkynyl group, an alkyl thioether-containing alkyl group, a heterocyclic group-containing alkyl thioether group, a hydrocarbon ring group-containing alkyl ether group and an alkyloxycarbonyl group and is the one exemplified for $R^1$ as above. Among these, $R^7$ is preferably selected from a cyclohexyl group, a phenyl group, a naphthyl group, a furyl group, a phenethyl group, a benzyloxyethyl group and an alkyloxycarbonyl group.

In the chemical reaction formula (VI), the proline derivative (1) acts as a catalyst and is used at, relative to the substrate α,β-unsaturated nitro compound (3), preferably 1 to 50 mol % and more preferably 10 mol %. In the chemical reaction formula (VI), the proline derivative (1) is exemplified by (S)-diphenylprolinol trimethylsilyl ether; however it is not particularly limited as far as it is an optically active proline derivative and is represented by the chemical formula (I). Preferably, the proline derivative (1) is solely one of enantiomers.

In the chemical formula (III), $R^2$ is a carboxyl group, a tetrazole group or a —$C(R^4)(R^5)OR^6$ group [wherein $R^4$ and $R^5$ respectively and independently may contain a substituent and are a hydrocarbon aromatic ring group such as a phenyl group and a naphthyl group; a heteroaromatic ring group such as a pyridyl group, an imidazolyl group and a thiazolyl group; or a linear, branched and/or cyclic alkyl group containing 1 to 4 carbon atoms, e.g. a methyl group, an ethyl group, a propyl group, an isopropyl group, a butyl group or a tert-butyl group; and $R^6$ is a hydrogen atom; a silyl group such as a trimethoxysilyl group, a triethylsilyl group, a tert-butyldimethylsilyl group, a triisopropylsilyl group and a tert-butyldiphenylsilyl group; or a linear, branched and/or cyclic alkyl group containing 1 to 4 carbon atoms, e.g. a methyl group, an ethyl group, a propyl group, an isopropyl group, a butyl group or a tert-butyl group]; $R^3$ represents a protective group such as an alkyl group, an acetyl group and a silyl group; and n represents a number of 0 to 1, preferably an integer of 0 or 1.

This asymmetrical catalyst, proline derivative (1), can be produced from a starting material of an optically active proline or a derivative thereof (such as 3-hydroxyproline and 4-hydroxyproline) according to, for example, H. Gotoh et al., Angewandte Chemie International Edition, 2006, vol. 45, p. 6853-6856 and H. Gotoh et al., Organic Letters, 2007, vol. 9, p. 2859-2862.

The substituent which $R^1$, $R^4$, $R^5$ and $R^7$ may contain is not particularly limited as far as it does not inhibit the Michael-Henry reaction and may include a linear, branched and/or cyclic alkyl group containing 1 to 4 carbon atoms, e.g. a methyl group, an ethyl group, a propyl group, an isopropyl group, a butyl group, a tert-butyl group, a cyclopropyl group or a cyclobutyl group; a linear or branched alkoxy group containing 1 to 4 carbon atoms, e.g. a methoxy group, an ethoxy group, a propoxy group, an isopropoxy group, a butoxy group, an isobutoxy group or a tert-butoxy group; a carboxyl group; an aralkyl group such as a benzyl group or a phenethyl group; an ester group such as a methyl ester group, an ethyl ester group, a propyl ester group, an isopropyl ester group, a butyl ester group, an isobutyl ester group or a tert-butyl ester group; a hydroxyl group; a nitro group; a cyano group; and/or a halogen atom such as a fluorine, chlorine, bromine or iodine atom.

As used herein unless otherwise stated, among the symbols representing bond axes to functional groups from a five-membered ring,

,,,\\\ represents the configuration of the bond that projects below the plane of the paper (i.e. α-configuration), represents the configuration of the bond that projects above the plane of the paper (i.e. β-configuration), and represents the α-configuration, the β-configuration or the configuration where these configurations are present at certain proportions, as apparent to a person skilled in the art. The compound having a particular configuration indicated in the present invention is, however, not limited to a substantially pure single compound and may be the one which has the configuration predominantly.

The catalyst is exemplified by an asymmetrical catalyst, proline derivative (1). However, the catalyst may be a compound having a monocyclic or condensed pyrrolidine ring and an optically active α-carbon relative to the nitrogen on the ring. The α-carbon is preferably linked to a methylene group or a methine group. More specifically, the catalyst may include, in addition to the proline derivative (1), optically active compounds represented by the following chemical formulae and optical isomers thereof. In the formulae, Me indicates methyl, Et indicates ethyl, Pr indicates propyl, Bu indicates butyl, Ph indicates phenyl and Tf indicates trifluoromethylsulfonyl.

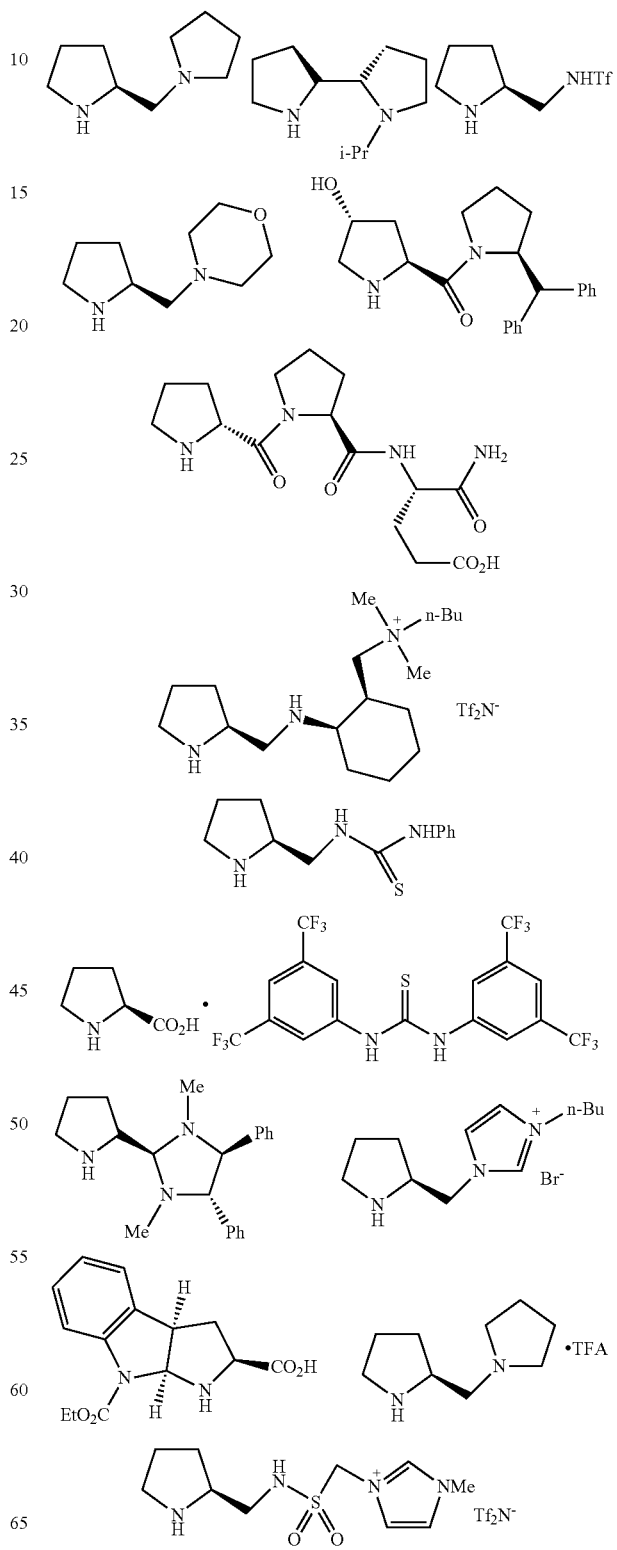

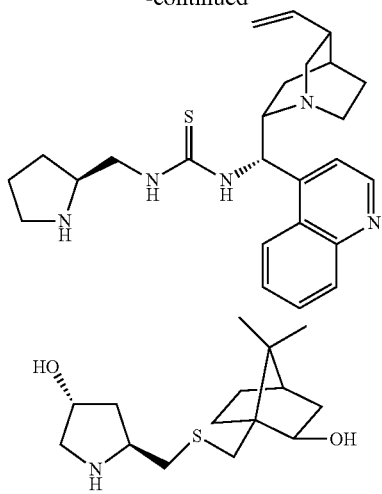

Among these, the catalyst is preferably a proline derivative because of the availability of optically active starting materials therefor and liability for functional conversion thereof to desired chiral compounds.

The cyclization step is preferably carried out in a water-insoluble organic solvent selected from a halogen-containing organic solvent, an aromatic organic solvent and a hydrocarbon organic solvent and/or a non-oxygen atom-containing water-soluble organic solvent that is a nitrile-substituted hydrocarbon organic solvent. The water-insoluble organic solvent may include a halogen-containing organic solvent such as a halogen hydrocarbon exemplified by dichloromethane, dichloroethane or chloroform; an aromatic organic solvent such as benzene, toluene, o-, m- or p-xylene; a hydrocarbon organic solvent such as pentane, hexane or heptane; and an acyclic ether organic solvent such as diethyl ether. The non-oxygen atom-containing water-soluble organic solvent may include a non-ethereal and non-alcoholic water-soluble organic solvent which does not contain an oxygen atom such as acetonitrile.

When the cyclization step is carried out in the water-insoluble organic solvent which has low polarity or the non-oxygen atom-containing water-soluble organic solvent, a five-membered ring-containing compound in which $R^1$ and the adjacent aldehyde group on the five-membered ring are solely in the cis form can be obtained with diastereoselectivity and with a high yield of over 70% and the optical yield of as high as 95% ee, despite the fact that the active sites for the Michael-Henry reaction in order to form a five-membered ring de novo are less accessible each other due to a large steric hindrance. It is inferred that the five-membered ring-containing compound in which $R^1$ and the aldehyde group are solely in the cis form is obtained because the cyclization in the Henry reaction undergoes through the transition state with the cis configuration and the aldehyde group is not isomerized even after the cyclization. Particularly the non-oxygen atom-containing water-soluble organic solvent such as acetonitrile can further stabilize the aldehyde group after the cyclization, and thus it is not required to stabilize the aldehyde group by reducing it to a hydroxymethyl group or subsequently protecting the aldehyde group.

On the other hand, carrying out the cyclization step in a water-soluble organic solvent having high polarity other than acetonitrile, e.g. in an organic solvent which is arbitrarily water miscible such as tetrahydrofuran (THF), methanol or 1,4-dioxane is not at all practical because even when the reaction time is prolonged, cyclization reaction may not proceed at all, or complicated by-products may result, or the five-membered ring-containing compound may be obtained with a very low yield of as low as a few percent.

It is inferred that there is a significant difference in the yield according to the difference in nature of the solvents because the water-insoluble organic solvent having low polarity and the water-soluble organic solvent which has high polarity but does not contain an oxygen atom stabilize the transition state during the Michael-Henry reaction in the cyclization step and facilitate the formation of a bond between the active sites.

The cyclization step is further preferably carried out in the presence of catalytic amounts of both the proline derivative (1) and an acid. The acid is preferably a free acid having the acid dissociation constant (pKa) at 25° C. in water of 2.5 to 11, still more preferably 4 to 10.

The acid may include a fatty acid derivative containing 1 to 4 carbon atoms, e.g. an aliphatic monocarboxylic acid derivative exemplified by acetic acid, n-propionic acid and butyric acid; a haloaliphatic monocarboxylic acid derivative exemplified by trifluoroacetic acid and chloroacetic acid; an aliphatic polycarboxylic acid derivative exemplified by oxalyl acid, d,l-tartaric acid, citric acid, succinic acid, malonic acid and cis-maleic acid; an aromatic carboxylic acid derivative, e.g. a benzoic acid derivative exemplified by benzoic acid, 3-hydroxybenzoate and 3-methylbenzoate; a heteroaromatic carboxylic acid derivative exemplified by nicotinic acid;

a hydroxyaromatic derivative, e.g. a phenol derivative exemplified by phenol, 2,4-dinitrophenol, 2-chloro-4-nitrophenol, 2,4,6-trichlorophenol, 2,6-dichlorophenol, 2,6-difluorophenol, 2,6-dimethyl-4-nitrophenol, 4-nitrophenol, 2-hydroxybenzonitrile, 2-nitrophenol, 2,3-dichlorophenol, 4-cyanophenol, 2,4-dichlorophenol, 2-hydroxy-benzamide, 3,5-dichlorophenol, 3-nitrophenol, 3,4-dichlorophenol, 2-chlorophenol, 3-cyanophenol, 4-chlorophenol, 3-methoxyphenol, 3-methylphenol, 3,5-dimethylphenol and 4-methylphenol; a hydroxynaphthalene derivative exemplified by 1-hydroxynaphthalene and 2-hydroxynaphthalene; and a perfluoroalkyl group-containing alcohol, e.g. 1,1,1,3,3,3-hexafluoro-2-propanol.

The acid may be a single species or more than one species in combination.

Among these acids, the acid having pKa of 6 to 8 at 25° C. in water is particularly preferable. The acid having pKa of 6 to 8 may include, for example, 2,4,6-trichlorophenol, cis-maleic acid, 2,6-dichlorophenol, 2,6-difluorophenol, 2,6-dimethyl-4-nitrophenol, 4-nitrophenol, 2-hydroxybenzonitrile, 2-nitrophenol, 2,3-dichlorophenol, 4-cyanophenol, 2,4-dichlorophenol, 2-hydroxy-benzamide and the like.

The cyclization step carried out in the presence of catalytic amounts of both the proline derivative (1) and the acid can provide an increased reaction speed, such that the cyclization step can be completed within a reduced time period as ⅓ to 1/24 of the time required for the reaction with the absence of the acid, and can provide an increased yield of the cyclization as well.

The proline derivative (1) and the acid are preferably present at a molar ratio of 1:1 to 1:2.

The reaction mechanism in the cyclization step where the 1,4-butanedione compound (2) and the α,β-unsaturated nitro compound (3) are derived to the cyclized five-membered ring-containing compound (7) using the asymmetrical proline derivative (1) as a catalyst by the Michael-Henry reaction is inferred as below by referring to the chemical reaction formula (VIII).

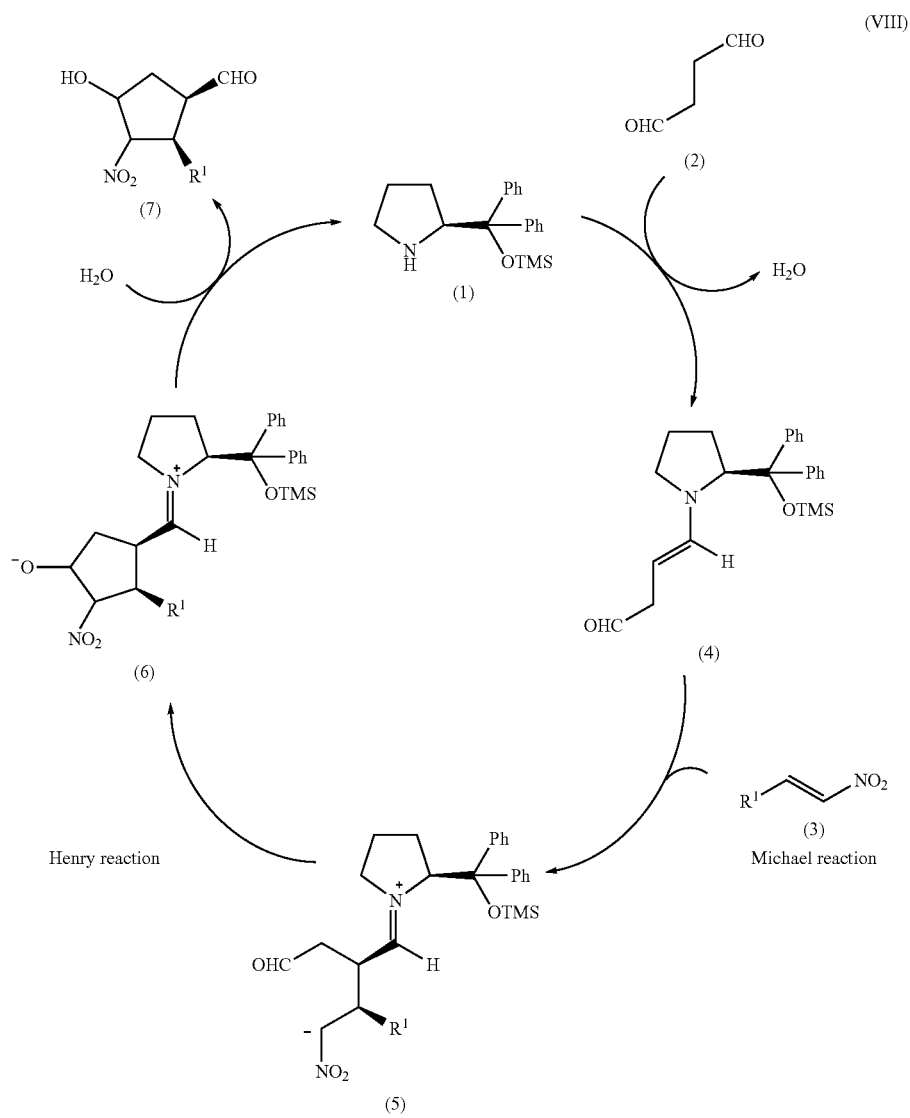

The 1,4-butanedione compound (2) is dehydrated due to the reaction thereof with the proline derivative (1) to produce an enamine (4), which then undergoes the Michael reaction with the α,β-unsaturated nitro compound (3), resulting in diastereoselective and enantioselective condensation thereof in the cis configuration to form a zwitter ion (5). The cyclization step carried out in the water-insoluble organic solvent having low polarity or the non-oxygen atom-containing water-soluble organic solvent having high polarity facilitates the formation of a bond between active sites and stabilizes the zwitter ion (5) which is the transition state during the Michael-Henry reaction. This steric benefit results in the conformation that may provide the cis configuration between the $R^1$ group and the group derived from the proline derivative upon cyclization. The nucleophilic nitrocarbanion in the zwitter ion (5) cyclizes by nucleophilic reaction with the electrophilic aldehyde group by the intramolecular Henry reaction so as to produce a cyclized five-membered ring-containing compound precursor (6) in which the $R^1$ group and the group derived from the proline derivative are in the cis configuration. Addition of water to the precursor (6) produces the cyclized five-membered ring-containing compound (7) together with the by-product, the proline derivative (1). The cyclized five-membered ring-containing compound (7) obtained is a diastereomer mixture in which the nitro group on the ring and a de novo adjacent hydroxyl group are in the relationship of cis/trans. The above step carried out in the concomitant presence of the acid further activates the α,β-unsaturated nitro compound (3) and facilitates the Michael reaction, resulting in the effects of the further increased yield, improved stereoselectivity and decreased reaction time and the like.

The cyclized five-membered ring-containing compound (7) which has the aldehyde group is not highly stable and is difficult to be maintained for a prolonged time. Thus the cyclized five-membered ring-containing compound (7), after or without isolation, may be subsequently reduced with a reducing agent to derive the reduced five-membered ring compound (8) for a temporary storage.

The reducing agent which is used for reduction of the cyclized five-membered ring-containing compound (7) to derive the reduced five-membered ring compound (8) is not particularly limited as far as it can reduce the aldehyde group to a hydroxymethyl group without inversion of the configuration, and is particularly preferably $NaBH_4$, $NaBH_3CN$, $B_2H_6$, $BH_3 \cdot (CH_3)_2S$, $LiAlH_4$, $NaB(O_2CCH_3)_3H$ or $LiBH(C_2H_5)_3$.

Optionally, the hydroxyl group on the ring of the reduced five-membered ring compound (8) may be dehydrated to be derived to a further stable nitrocyclopentene compound and/or a hydroxyl group on an acyclic radical of the reduced five-membered ring compound (8) may be protected with an acyl group, an alkyl group or an aralkyl group to derive an ester or ether compound. The treatment with acetic anhydride (Ac$_2$O) in the presence of pyridine causes acetylation and simultaneous dehydration to give an acetyl ester, nitrocyclopentene compound (9). From a mixture of four diastereomers in which the nitro group and the adjacent hydroxyl group on the ring of the reduced five-membered ring compound (8) are in the relationship of cis/trans, a single nitrocyclopentene compound (9) is obtained.

The cyclized five-membered ring-containing compound (7) and nitrocyclopentene compound (9) can derive PGs having desired physiological activities such as PGEs and PGFs by, as schematically shown in the chemical reaction formula (VII), the homologation reaction such as the Horner-Wadsworth-Emmons reaction, functional conversion reactions of the de novo carbonyl group such as reduction, acetylation and dehydration, as appropriate. The PGE (10-a), dehydroxy-PGE (10-b) and PGFα (10-c), for example, can be derived by the process shown in the following reaction process formula (IX). The cyclized five-membered ring-containing compound (7), after or without isolation, may be subjected to the homologation reaction of the aldehyde group by the Horner-Wadsworth-Emmons reaction or the Wittig reaction in one pot to produce a ω side chain group which is then appropriately subjected to functional conversion prior to the aside chain group formation in order to convert the functional group on the five-membered ring. The order of the functional conversions may be permutated.

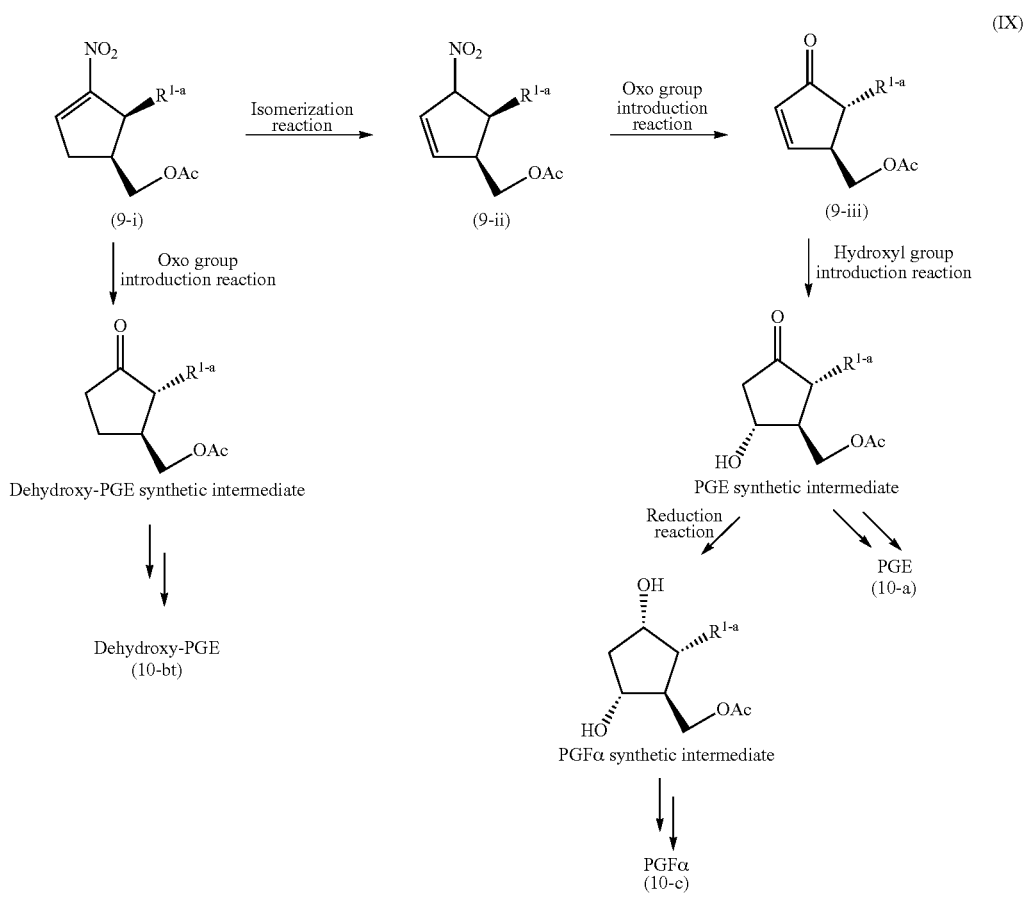

(IX)

More specifically, in the reaction process formula (IX), a compound represented by the chemical formula (9-ii):

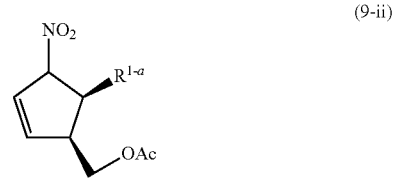

(9-ii)

wherein in the formula (9-ii), $R^{1-a}$ represents a functional group corresponding to the α chain of prostaglandin such as an alkyl group, an alkenyl group or an alkynyl group which contains a substituent such as a hydroxyl group, a carboxyl group or an ester group, and a derivative functional group which can be readily converted to the functional group corresponding to the α chain,
can be produced by subjecting the compound represented by the chemical formula (9-i):

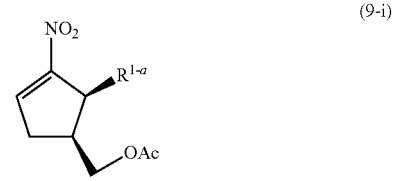

(9-i)

wherein R$^{1-a}$ has the same meaning as above,
to the isomerization reaction and optionally to deprotection reaction of a protective group in R$^{1-a}$.

The isomerization reaction is well known and is carried out, for example, in an organic solvent (acetonitrile, methanol, ethanol, isopropanol etc.) or a mixed solvent thereof with water, in the presence of an organic base (dimethylamine, triethylamine, 1,4-diazabicyclo[2.2.2]octane (DABCO), 1,8-diazabicyclo[5.4.0]undec-7-ene (DBU)) or an inorganic base (sodium hydrogen carbonate, sodium carbonate, potassium carbonate etc.) at a temperature of 0 to 100° C.

Deprotection reaction of the protective group can be carried out according to the following methods.

Deprotection reaction of a protective group of a hydroxyl or carboxyl group is well known and may include, for example,
(1) alkaline hydrolysis,
(2) deprotection reaction under an acidic condition,
(3) deprotection reaction by hydrogenolysis,
(4) deprotection reaction of a silyl group
and the like.

Specifically, the deprotection reactions are described as follows.

(1) Deprotection reaction by alkaline hydrolysis is carried out, for example, in an organic solvent (methanol, tetrahydrofuran, dioxane or a mixed solvent thereof), by using an alkali metal hydroxide (sodium hydroxide, potassium hydroxide, lithium hydroxide etc.), an alkaline earth metal hydroxide (barium hydroxide, calcium hydroxide etc.) or a carbonate salt (sodium carbonate, potassium carbonate etc.) or an aqueous solution thereof or a mixture thereof at a temperature of 0 to 40° C.

(2) Deprotection reaction under an acidic condition is carried out, for example, in an organic solvent (methylene chloride, chloroform, dioxane, ethyl acetate, anisole, methanol, ethanol, isopropyl alcohol etc.) or in the absence of the organic solvent or in an aqueous solution thereof and in an organic acid (acetic acid, trifluoroacetic acid, methanesulfonic acid etc.), an inorganic acid (hydrochloric acid, sulfuric acid etc.) or a mixture thereof (hydrogen bromide/acetic acid etc.) at a temperature of 0 to 100° C.

(3) Deprotection reaction by hydrogenolysis is carried out, for example, in a solvent (ether-based (tetrahydrofuran, dioxane, dimethoxyethane, diethyl ether etc.), alcohol-based (methanol, ethanol etc.), benzene-based (benzene, toluene etc.), ketone-based (acetone, methyl ethyl ketone, etc.), nitrole-based (acetonitrile etc.), amide-based (dimethylformamide etc.), water, ester-based (ethyl acetate etc.), acetic acid or a mixed solvent of two or more of these), in the presence of a catalyst (palladium-carbon, palladium black, palladium hydroxide, platinum oxide, Raney nickel etc.), in a hydrogen atmosphere or in the presence of ammonium formate under normal or increased pressure at a temperature of 0 to 200° C.

(4) Deprotection reaction of a silyl group is carried out, for example, in a water-miscible organic solvent (tetrahydrofuran, acetonitrile etc.), by using tetrabutylammonium fluoride at a temperature of 0 to 40° C.

The protective group of a hydroxyl group may include, for example, a methoxymethyl group, a 2-tetrahydropyranyl group, a t-butyldimethylsilyl group, a t-butyldiphenylsilyl group, an acetyl group, a benzyl group, a 4-methoxybenzyl group, a pivaloyl group and the like.

The protective group of a carboxyl group may include, for example, a methyl group, an ethyl group, a propyl group, an isopropyl group, a t-butyl group and the like.

The protective group of a hydroxyl or carboxyl group is not particularly limited to those described above as far as it can be readily and selectively eliminated. For example, those described in T. W. Greene, Protective Groups in Organic Synthesis 3rd edition, Wiley, New York, (1999) may be used.

A person skilled in the art readily understands that, by using these deprotection reactions according to needs, a compound such as a desired PG synthetic intermediate (10) can be conveniently produced.

In the reaction process formula (IX), a compound represented by the chemical formula (9-11i):

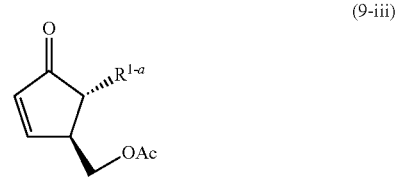

(9-iii)

wherein R$^{1-a}$ has the same meaning as above,
can be produced by subjecting the compound represented by the chemical formula (9-ii) to oxo group introduction reaction and optionally to deprotection reaction of a protective group.

The oxo group introduction reaction is well known and is carried out, for example, in an organic solvent (acetonitrile, tetrahydrofuran, methanol, ethanol, isopropanol etc.) or a mixed solvent thereof with water, in the presence of an organic base (dimethylamine, triethylamine, 1,4-diazabicyclo[2.2.2]octane (DABCO), 1,8-diazabicyclo[5.4.0]undec-7-ene (DBU)) or an inorganic base (sodium hydrogen carbonate, sodium carbonate, potassium carbonate etc.) at a temperature of 0 to 100° C., or in an organic solvent (acetonitrile, methanol, ethanol, isopropanol etc.) or a mixed solvent thereof with water and in an organic acid (acetic acid, trifluoroacetic acid, methanesulfonic acid etc.), an inorganic acid (hydrochloric acid, sulfuric acid etc.) or a mixture thereof (hydrogen bromide/acetic acid etc.) at a temperature of 0 to 100° C. Optionally, metal (zinc etc.) may be added.

Deprotection reaction of the protective group can be carried out by the same manner as described above.

In the reaction process formula (IX), a compound represented as the PGE synthetic intermediate:

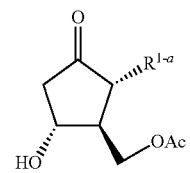

PGE synthetic intermediate
wherein R$^{1-a}$ has the same meaning as above,
can be produced by subjecting the compound represented by the chemical formula (9-11i) to hydroxyl group introduction reaction and optionally deprotection reaction of a protective group.

The hydroxyl group introduction reaction is well known and a hydroxyl group can be introduced by, for example, carrying out epoxidation reaction in an organic solvent (benzene, toluene etc.) or a mixed solvent thereof with water, with an oxidizing agent added (sodium hypochlorite, meta-chloroperbenzoic acid, Oxon®, t-butyl hydroperoxide, hydrogen peroxide etc.) at a temperature of 0 to 40° C. and subjecting the obtained epoxidized compound to ring-opening reaction in an organic solvent (acetonitrile, tetrahydrofuran, toluene, methanol, ethanol etc.) or a mixed solvent thereof with water, in the presence of tetrabutyl tin hydride, a metal (zinc etc.) and a salt (sodium dithionite, ammonium chloride etc.) at a temperature of 0 to 100° C.

Deprotection reaction of the protective group can be carried out by the same manner as described above.

The PGE (10-a) can be produced by further subjecting the PGE synthetic intermediate to a well known reaction.

In the reaction process formula (IX), a compound represented as the PGFα synthetic intermediate:

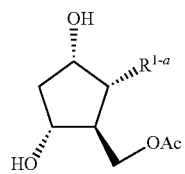

PGFα synthetic intermediate
wherein $R^{1-a}$ has the same meaning as above,
can be produced by subjecting the compound represented as the PGE synthetic intermediate to reduction reaction and optionally deprotection reaction of a protective group.

The reduction reaction is well known and can be carried out, for example, in an organic solvent (methanol, ethanol, tetrahydrofuran, benzene, toluene etc.) by adding a reducing agent (sodium borohydride, LiBH (sec-$C_4H_9$)$_3$ such as L-Selectride®, $NaBH_3CN$, $B_2H_5$, $BH_3$—$(CH_3)_2S$, $LiAlH_4$, $NaB(O_2CCH_3)_3H$, $LiBH(C_2H_5)_3$ etc.) at a temperature of 0 to 40° C.

Deprotection reaction of the protective group can be carried out by the same manner as described above.

The PGFα (10-c) can be produced by further subjecting the PGFα synthetic intermediate to a well known reaction.

In the reaction process formula (IX), a compound represented as the dehydroxy-PGE synthetic intermediate:

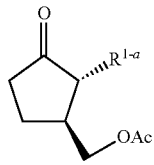

Dehydroxy-PGE synthetic intermediate
wherein $R^{3-a}$ has the same meaning as above,
can be produced by subjecting the compound represented by the chemical formula (9-i) to oxo group introduction reaction and optionally deprotection reaction of a protective group.

The oxo group introduction reaction can be carried out by the same manner as described above.

Deprotection reaction of the protective group can be carried out by the same manner as described above.

The dehydroxy-PGE (10-c) can be produced by subjecting the dehydroxy-PGE synthetic intermediate to a well known reaction.

Among the compounds represented as the nitrocyclopentene compound (9), the nitrocyclopentene compound wherein $R^1$ is $(CH_2)_6COOC_2H_5$, i.e. the compound (9-i-a) can derive $PGE_1$ according to the following reaction process formula (X).

(X)

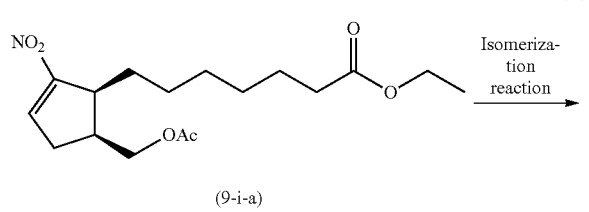

(9-i-a)

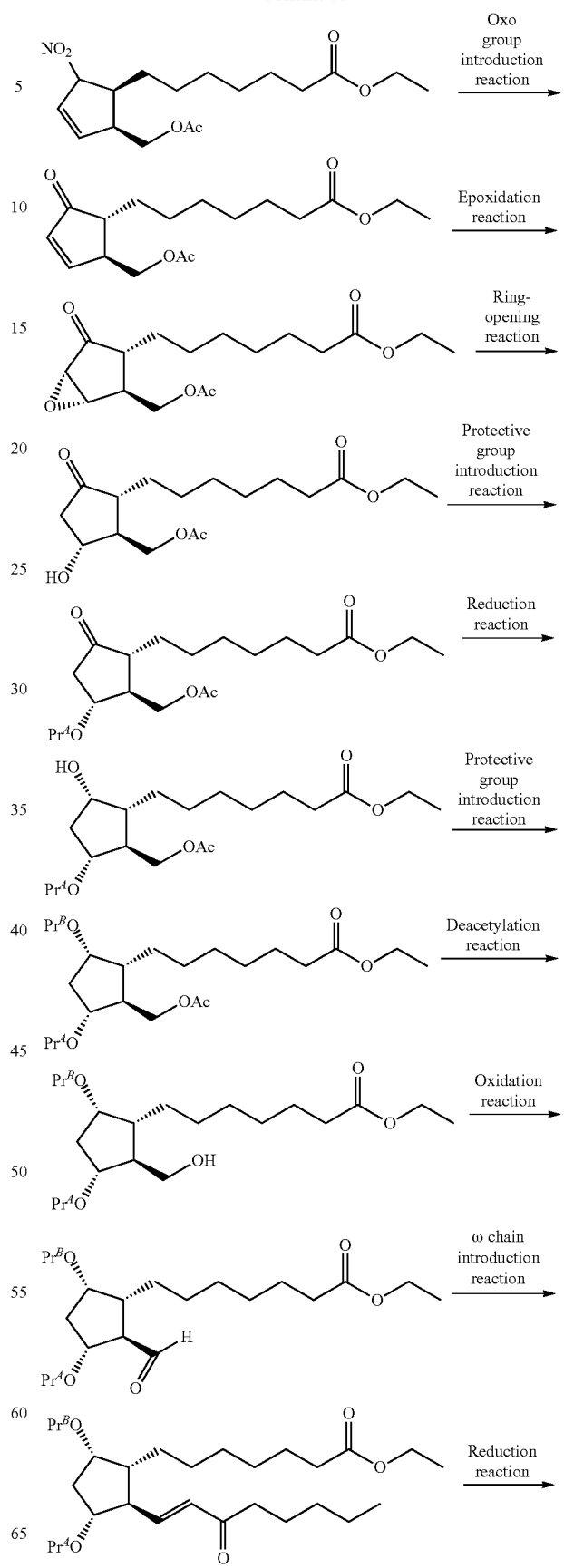

-continued

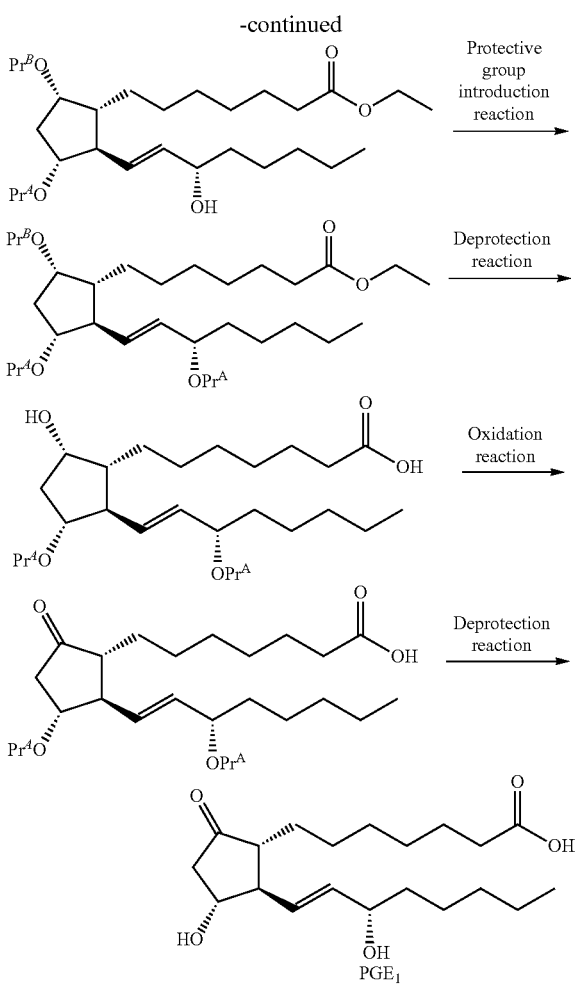

(In the formula (X), $Pr^A$ and $Pr^B$ are the same or different from each other and respectively represent a protective group of the hydroxyl group.)

The reactions shown in the reaction process formula (X) can be carried out according to the methods described for the reaction process formula (IX) or the methods pursuant thereto.

In the reactions described herein, reaction products can be purified by means of a conventional purification means, for example, distillation under normal or reduced pressure, high performance liquid chromatography, thin-layer chromatography or column chromatography using silica gel or magnesium silicate as a carrier, or washing and recrystallization and the like. Purification may be carried out after each reaction or after some reactions.

When the proline derivative (1) used is an enantiomeric optically active substance, the other enantiomer can be obtained. Although the proline derivative (1) is exemplified, when another catalyst which has a pyrrolidine ring and an optically active α-carbon relative to the nitrogen on the ring is used that is an enantiomeric optically active substance, an enantiomer is enantioselectively obtained.

EXAMPLES

Examples of the method for producing a five-membered ring-containing compound to which the present invention is applied and Comparative Examples of the method to which the present invention is not applied are specifically described hereinafter.

Example 1-1 Cyclization Step and Reduction Step

Under an argon atmosphere, to a solution of a nitrostyrene, i.e. (E)-(2-nitrovinyl)benzene (3a) (40.3 mg, 0.41 mmol) as the α,β-unsaturated nitro compound, succinaldehyde (2a) (53.4 mg, 0.62 mmol) as the 1,4-butanedione compound and p-nitrophenol (5.7 mg, 0.041 mmol) as the acid in $CH_2Cl_2$ (0.41 mL) as the water-insoluble organic solvent was added (S)-2-(diphenyl((trimethylsilyl)oxy)methyl)pyrrolidine (1a) (13.3 mg, 0.041 mmol) as the proline derivative at a room temperature (23° C.). The concentration of the substrate, nitrobenzene, in this solution was 1 M. This reaction solution was stirred at the same temperature for 3 hours. The main products were visualized as a diastereomer mixture by silica gel thin-layer chromatography (TLC) with the spots of reaction products (7a) at the Rf values=0.42, 0.32 and 0.23 (developing solvent:ethyl acetate:hexane=1:3). After confirming the elimination of the spot of nitrostyrene by TLC, the reaction solution was cooled to 0° C. and added with methanol (0.82 mL) and $NaBH_4$ (46.5 mg, 1.23 mmol). After stirring at 0° C. for 20 minutes, 1 N hydrochloric acid was added to terminate the reaction and the organic matter was extracted with chloroform 5 times. The combined organic layer was washed with a saturated aqueous sodium chloride solution and dried with magnesium sulfate. Low-boiling organic compounds such as solvents were distilled off under reduced pressure prior to purification of the obtained crude product by silica gel column chromatography (elution solvent:ethyl acetate:hexane=1:3→2:1) to obtain a desired reduced five-membered ring compound which is a diol, (3S,4R)-4-(hydroxymethyl)-2-nitro-3-phenylcyclopentanol (8a) (69.1 mg, 0.29 mmol), as a mixture of four diastereomers in which the configurations between the hydroxyl group and the nitro group were varied (0.37:1.00:0.98:0.46) with the yield of 71%. The results are shown in the following Table 1.

The results of physical and chemical analyses of the product by $^1H$ nuclear magnetic resonance spectrometry ($^1H$ NMR) and TLC are shown hereinbelow. The results of physical and chemical analyses support the chemical structure of 8a which is the mixture of four diastereomers.

$^1H$ NMR (CDCl$_3$) δ 2.03-2.10 (1.1H, m), 2.23 (1.9H, dd, J=8.0, 16.0 Hz), 2.40-2.48 (0.5H, m), 2.48-2.60 (0.5H, m), 3.48-3.56 (1H, m), 3.59-3.71 (1H, m), 3.37-3.48 (0.5H, m), 3.94-4.02 (0.5H, m), 4.62-4.70 (0.15H, m), 4.76 (0.36H, dd, J=5.6, 11.2 Hz), 4.85 (0.36H, dd, J=5.6, 9.6 Hz), 4.93 (0.13H, dd, J=4.4, 10.8 Hz), 7.21-7.40 (5H, m)

TLC: Rf=0.25 (36%), 0.31 (36%), 0.44 (15%), 0.55 (13%) (developing solvent:ethyl acetate:hexane=2:1) (the ratio of diastereomers was determined based on the integrated ratio from $^1H$ NMR)

Example 1-2 Dehydration Step

Under an argon atmosphere, a solution of the mixture of diastereomers (69.1 mg, 0.29 mmol) of the diol obtained from the cyclization step and the reduction step, (3S,4R)-4-(hydroxymethyl)-2-nitro-3-phenylcyclopentanol (8a) (69.1 mg, 0.29 mmol), in pyridine (0.58 mL) was cooled to 0° C., added with acetic anhydride ($Ac_2O$, 82.2 μL, 0.87 mmol) and stirred at the same temperature for 6 hours. The solution was further stirred at a room temperature for 12 hours. After addition of a phosphate buffer to terminate the reaction, the organic matter was extracted with ethyl acetate 3 times. The combined organic layer was washed with a saturated aqueous sodium chloride solution and dried with magnesium sulfate. Low-boiling organic compounds such as solvents were distilled off under reduced pressure prior to purification by silica gel column chromatography (elution solvent:ethyl acetate:hexane=1:10) to obtain a desired nitrocyclopentene compound which is a dehydrated substance, ((1R,2S)-3-nitro-2-phenylcyclopent-3-en-1-yl)methyl acetate (9a) (56.8 mg, 0.22 mmol) with the yield of 75%. The optical yield thereof which was determined by high performance liquid chromatography using a chiral column as the enantiomeric excess was 95% ee. The results are shown in the following Table 2.

The results of physical and chemical analyses of the product by $^1$H NMR, $^{13}$C NMR, infrared absorption spectrometry (IR), electrospray ionization high-resolution mass spectrometry (HRMS (ESI)), optical rotation measurement, optical purity measurement using a chiral column and Rf measurement by TLC are shown hereinbelow. The results of physical and chemical analyses support the chemical structure of 9a which is a single isomer.

$^1$H NMR (CDCl$_3$) δ 2.06 (3H, s), 2.44 (1H, bdt, J=4.4, 19.2 Hz), 2.67-2.78 (1H, m), 2.92 (1H, ddt, J=2.8, 8.8, 19.2 Hz), 4.11 (1H, dd, J=6.8, 11.2 Hz), 4.17-4.20 (1H, m), 4.18 (1H, dd, J=6.8, 11.2 Hz), 7.05 (2H, dd, J=2.4, 9.2 Hz), 7.11-7.21 (3H, m), 7.28-740 (2H, m);

$^{13}$C NMR (CDCl$_3$) δ 20.8, 32.5, 46.4, 51.4, 65.8, 126.8 (2C), 127.4, 129.0 (2C), 137.7, 140.7, 153.7, 170.9;

IR (neat) ν 1740, 1510, 1362, 1236, 1036, 755.9, 701.0 cm$^{-1}$;

HRMS (ESI): [M+Na]$^+$ calculated for C$_{13}$H$_{15}$NO$_5$Na: 284.0899. found: 284.0886;

$[α]_D^{13}$+116 (c 0.49, CHCl$_3$);

Optical yield: 95% ee (optical yield was such that when analyzed by high performance liquid column chromatography using a Chiralpak IB column (Daicel Corporation) with an elution solvent (hexane:isopropanol=80:1) at an elution speed of 1.0 mL/min, the major enantiomer had $t_R$=18.1 min and the minor enantiomer had $t_R$=19.4 min);

TLC: Rf=0.35 (developing solvent:ethyl acetate:hexane=1:3)

Example 2-1 to Example 2-2

The cyclization step and the reduction step were carried out in the same manner as Example 1-1 except that for the reaction conditions in the cyclization step, the water-insoluble organic solvent used was n-hexane and the conditions used were as shown in the following Table 1 to obtain a desired reduced five-membered ring compound which is a diol, (3S, 4R)-4-(hydroxymethyl)-2-nitro-3-phenylcyclopentanol (8a) as a mixture of four diastereomers in which the configurations between the hydroxyl group and the nitro group were varied. The diastereo ratio which was measured in the same manner as in Example 1-1 was TLC: Rf=0.25 (15%), 0.31 (34%), 0.44 (35%), 0.55 (16%) (developing solvent:ethyl acetate:hexane=2:1) (the ratio of diastereomers was determined based on the integrated ratio from $^1$H NMR). The results are summarized in Table 1. The dehydration step was carried out in the same manner as in Example 1-2 to obtain a desired nitrocyclopentene compound which is a hydrated substance, ((1R, 2S)-3-nitro-2-phenylcyclopent-3-en-1-yl)methyl acetate (9a) with the yield of 75% and the optical yield of 94% ee. The results are summarized in Table 2. Similar results of physical and chemical analyses were obtained.

TABLE 1

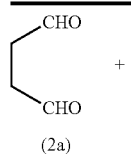

(2a)

TABLE 1-continued

Succinal-dehyde (2a) (eq.) | Cyclization step | | |
--- | --- | --- | ---
 | Solvent | Reaction temp. | Reaction time (h) | Yield (%)
Ex. 1-1 | 2.5 | CH$_2$Cl$_2$ (1M) | Room temp. | 3 | 71
Ex. 2-1 | 2.5 | n-Hexane (1M) | Room temp. | 22 | 47

TABLE 2

| | Product (9) | Yield (%) | Optical yield (% ee) |
--- | --- | --- | ---
Ex. 1-2 | (9a) | 75 | 95
Ex. 2-2 | (9a) | 75 | 94

As apparent from Table 1, when the cyclization step is carried out in the water-insoluble organic solvent such as dichloromethane (CH$_2$Cl$_2$) or hexane as Examples to which the present invention is applied, the reaction proceeds in a short time and the total yield from the cyclization step and the reduction step is as extremely high as 47 to 71%. As apparent from Table 2 as well, the yield from the dehydration step is as extremely high as 75% and the single diastereomer product is obtained with a high optical yield of 94 to 95% ee. Therefore it is demonstrated that the present invention can provide excellent stereoselectivity in terms of diastereoselectivity and enantioselectivity in the cyclization step.

Examples 3 to 4

By the similar manner as in Example 1-1 (Cyclization step and reduction step) except that, in the cyclization step, p-nitrophenol as the acid was not used and the conditions used for the water-insoluble organic solvent and the reaction time were as shown in Table 3, a desired reduced five-membered ring compound which is a diol, (3S,4R)-4-(hydroxymethyl)-2-nitro-3-phenylcyclopentanol (8a) was similarly obtained as a mixture of four diastereomers in which the configurations between the hydroxyl group and the nitro group were varied. The results are summarized in Table 3. Similar results of physical and chemical analyses were obtained.

Comparative Examples 1 to 3

The reactions were carried out in the similar manner as in Example 1-1 (Cyclization step and reduction step) except that, in the cyclization step, p-nitrophenol as the acid was not used, water-soluble cyclic ethers such as THF and dioxane or various oxygen atom-containing water-soluble solvents which are water-soluble alcohols such as methanol were used instead of the water-insoluble organic solvent and the condition used for the reaction time was as shown in Table 3. The results are summarized in Table 3.

the reaction rate tends to be low compared to the rate when the acid is used. The products were subjected to the dehydration step as Example 1-2 to similarly obtain a desired nitrocyclopentene compound which is a dehydrated substance, ((1R,2S)-3-nitro-2-phenylcyclopent-3-en-1-yl)methyl acetate (9a).

On the other hand, when the reaction is carried out in a water-soluble organic solvent such as THF, methanol and dioxane in the absence of the acid, the reaction does not proceed at all even with a prolonged period of time or, if any reaction proceeds, complicated by-products are produced and the five-membered ring-containing compound is obtained with a very low yield of at most a few percent.

Examples 5 to 12

The reactions were carried out in the same manner as Example 1-1 except that the reaction conditions used were as shown in Table 4. The results are summarized in Table 4.

TABLE 3

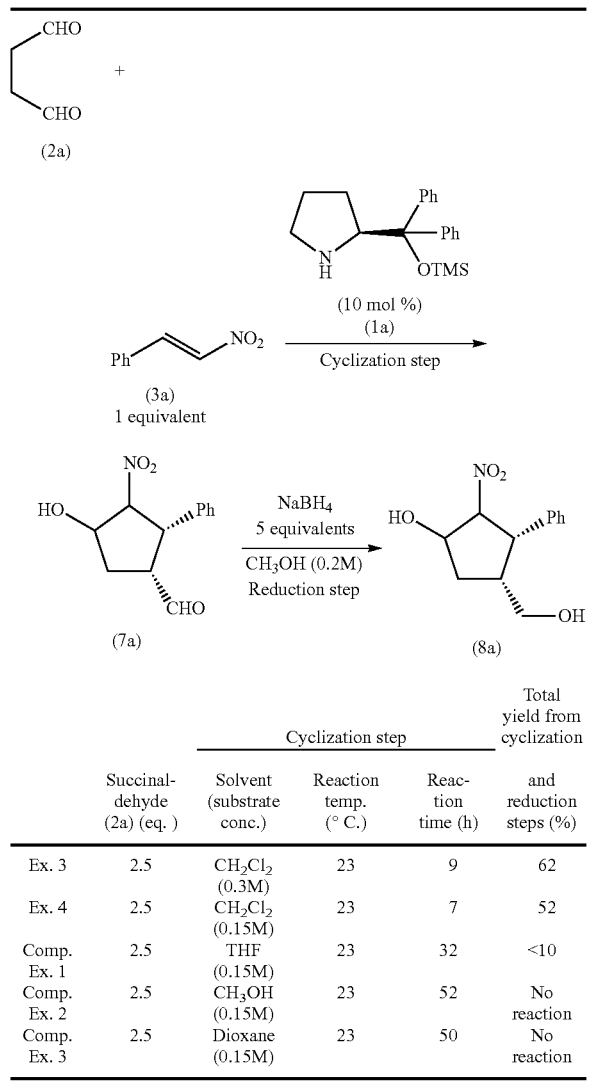

| | Succinaldehyde (2a) (eq.) | Solvent (substrate conc.) | Reaction temp. (° C.) | Reaction time (h) | Total yield from cyclization and reduction steps (%) |
|---|---|---|---|---|---|
| | | Cyclization step | | | |
| Ex. 3 | 2.5 | CH$_2$Cl$_2$ (0.3M) | 23 | 9 | 62 |
| Ex. 4 | 2.5 | CH$_2$Cl$_2$ (0.15M) | 23 | 7 | 52 |
| Comp. Ex. 1 | 2.5 | THF (0.15M) | 23 | 32 | <10 |
| Comp. Ex. 2 | 2.5 | CH$_3$OH (0.15M) | 23 | 52 | No reaction |
| Comp. Ex. 3 | 2.5 | Dioxane (0.15M) | 23 | 50 | No reaction |

As apparent from Table 3, the reaction proceeds in a relatively short time when it is carried out in the water-insoluble organic solvent such as dichloromethane despite the absence of the acid and the total yield from the cyclization step and the reduction step is as extremely high as 52 to 62%. However,

TABLE 4

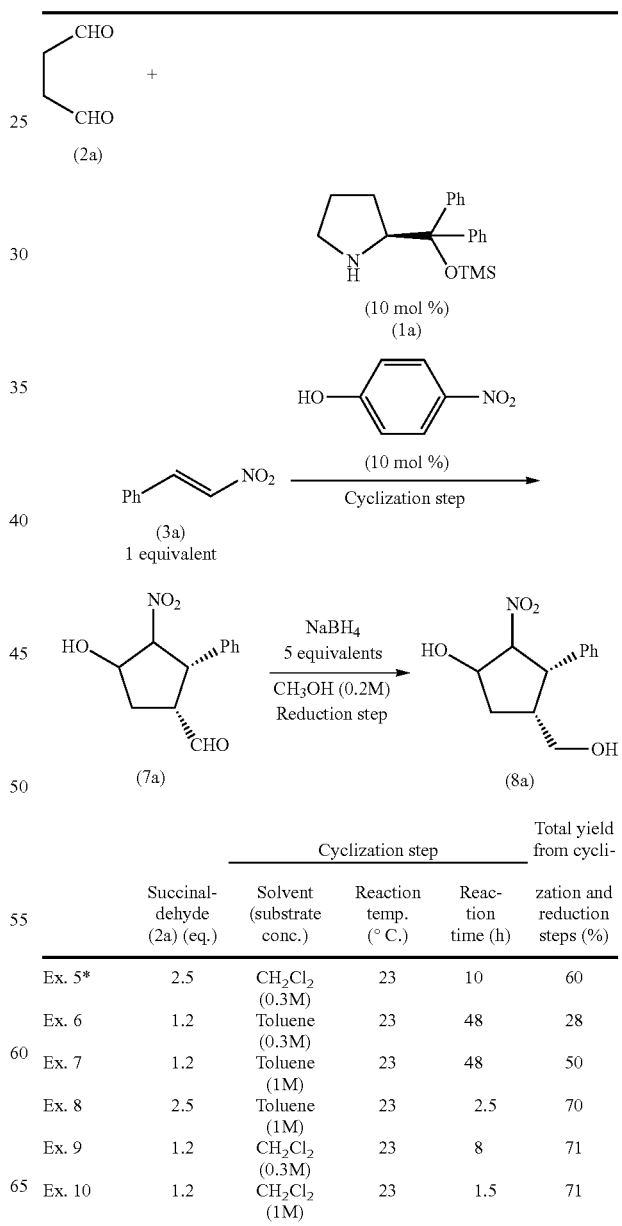

| | Succinaldehyde (2a) (eq.) | Solvent (substrate conc.) | Reaction temp. (° C.) | Reaction time (h) | Total yield from cyclization and reduction steps (%) |
|---|---|---|---|---|---|
| | | Cyclization step | | | |
| Ex. 5* | 2.5 | CH$_2$Cl$_2$ (0.3M) | 23 | 10 | 60 |
| Ex. 6 | 1.2 | Toluene (0.3M) | 23 | 48 | 28 |
| Ex. 7 | 1.2 | Toluene (1M) | 23 | 48 | 50 |
| Ex. 8 | 2.5 | Toluene (1M) | 23 | 2.5 | 70 |
| Ex. 9 | 1.2 | CH$_2$Cl$_2$ (0.3M) | 23 | 8 | 71 |
| Ex. 10 | 1.2 | CH$_2$Cl$_2$ (1M) | 23 | 1.5 | 71 |

TABLE 4-continued

| Ex. 11 | 1.5 | CH$_2$Cl$_2$ (1M) | 0 | 2.5 | 74 |
| Ex. 12 | 1.5 | CH$_2$Cl$_2$ (1M) | 23 | 2 | 69 |

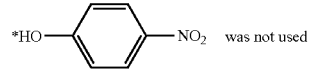 was not used

As apparent from Table 4, the reaction proceeds in a relatively short time when it is carried out in the water-insoluble organic solvent such as dichloromethane and toluene and the total yield from the cyclization step and the reduction step is extremely high. The products were subjected to the dehydration step as Example 1-2 to similarly obtain a desired nitrocyclopentene compound which is a dehydrated substance, ((1R,2S)-3-nitro-2-phenylcyclopent-3-en-1-yl)methyl acetate (9a). The optical yield after the dehydration step for Example 5 was 91% ee and that for Example 11 was 95% ee and other Examples also had approximately similar values.

Example 13-1 to Example 21-1

By the similar manner as in Example 1-1 (Cyclization step and reduction step) except that the reaction conditions used were as shown in Table 5, desired reduced five-membered ring compounds which were diol products (8a to 8i) were obtained respectively as mixtures of four diastereomers in which the configurations between the hydroxyl group and the nitro group were varied. The results are summarized in Table 5. The results of physical and chemical analyses of the obtained mixtures of diastereomers by $^1$H NMR and TLC are shown hereinbelow. The results of physical and chemical analyses of (8a) were the same as those obtained before and the results for (8b to 8i) support the chemical structures of 8b to 8i which are mixtures of four diastereomers.

TABLE 5

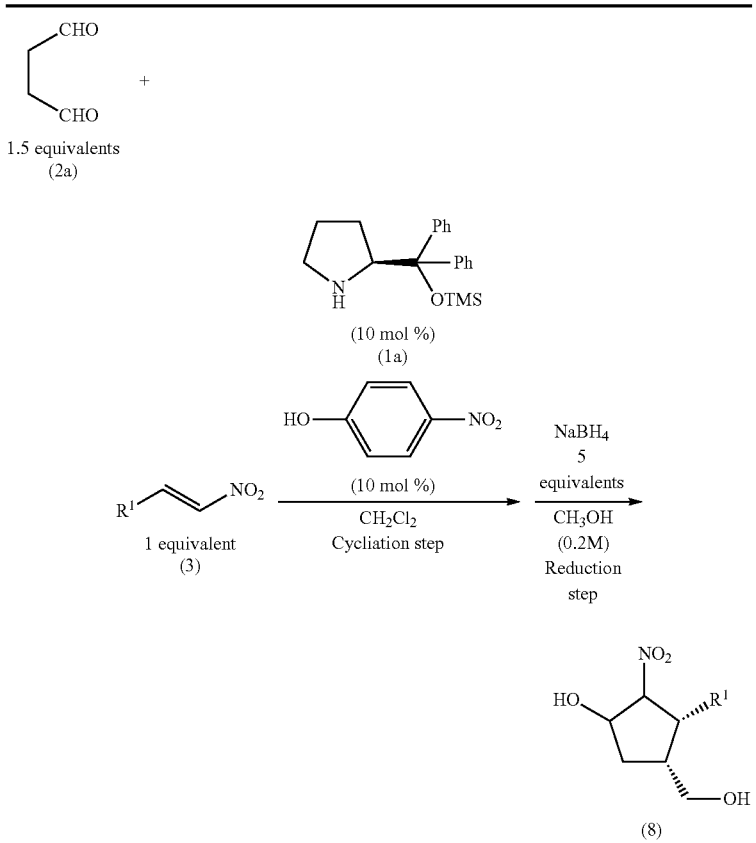

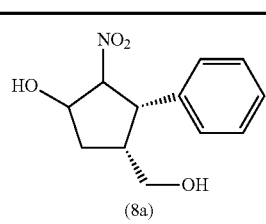

TABLE 5-continued
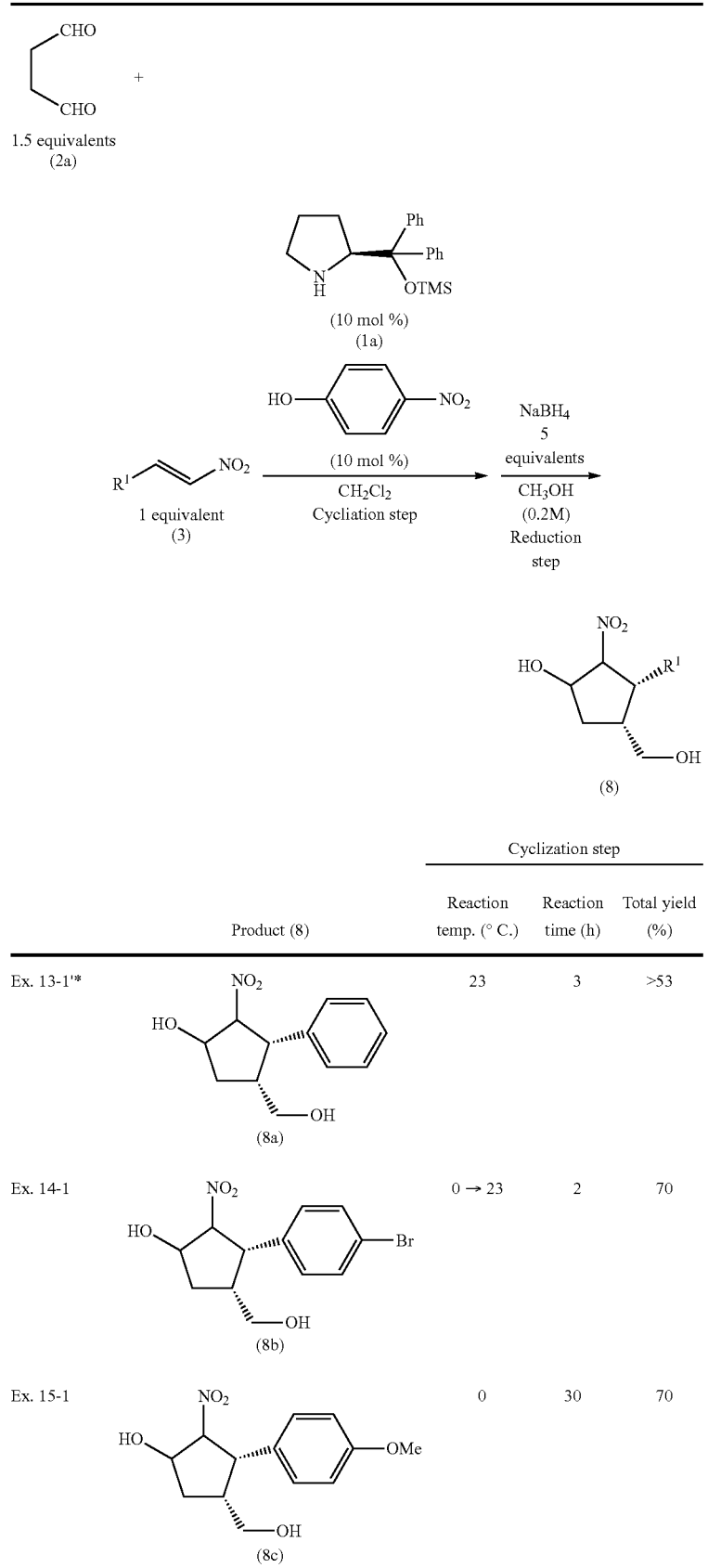

TABLE 5-continued
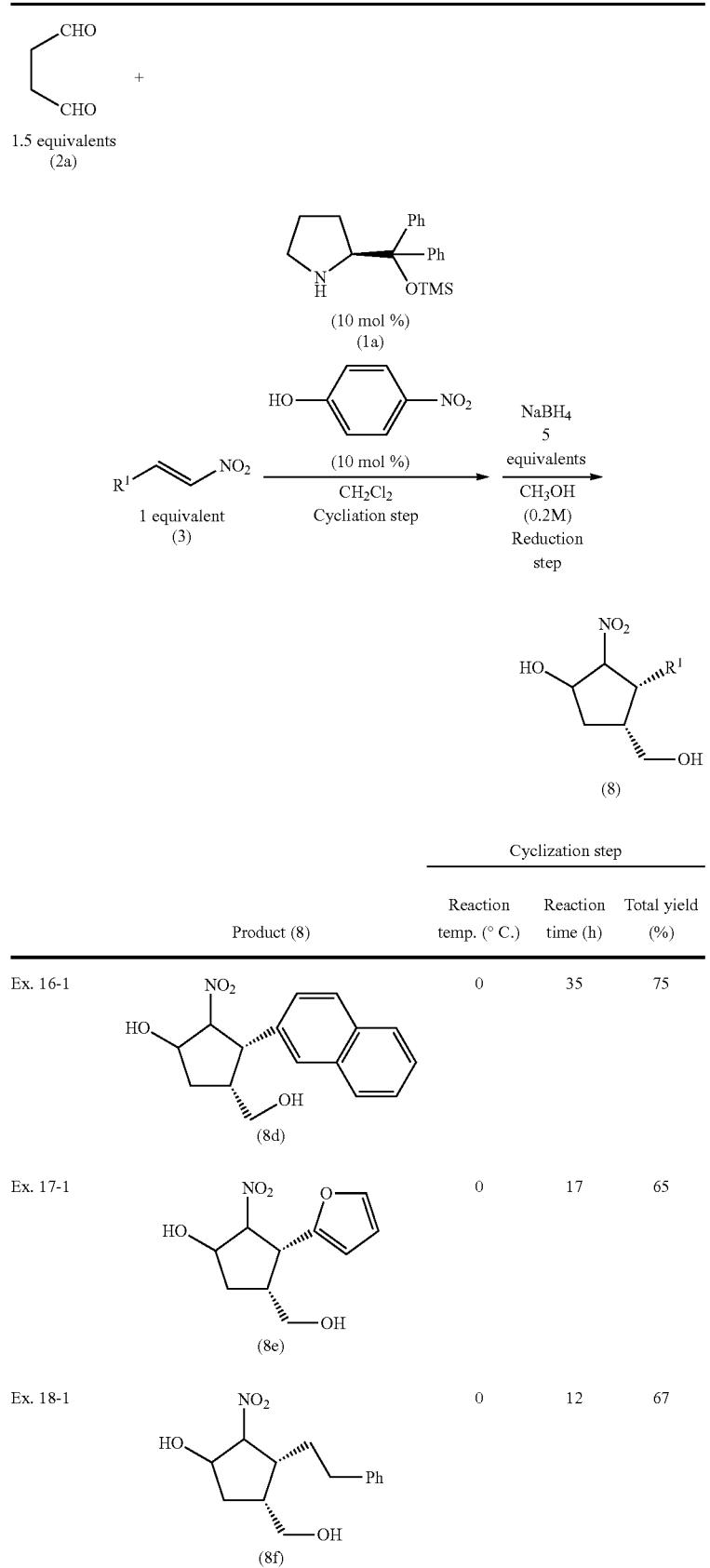
|  | Product (8) | Cyclization step | | |
|---|---|---|---|---|
|  |  | Reaction temp. (° C.) | Reaction time (h) | Total yield (%) |
| Ex. 16-1 | (8d) | 0 | 35 | 75 |
| Ex. 17-1 | (8e) | 0 | 17 | 65 |
| Ex. 18-1 | (8f) | 0 | 12 | 67 |

TABLE 5-continued
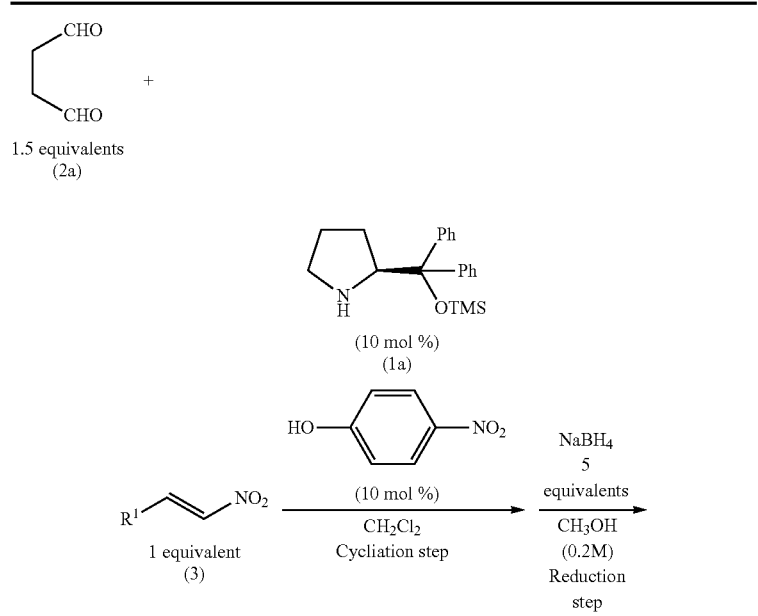
| | Product (8) | Cyclization step | | |
|---|---|---|---|---|
| | | Reaction temp. (° C.) | Reaction time (h) | Total yield (%) |
| Ex. 19-1** | (8g) | 0 | 6 | 82 |
| Ex. 20-1*** | (8h) | 23 | 17 | 49 |

TABLE 5-continued

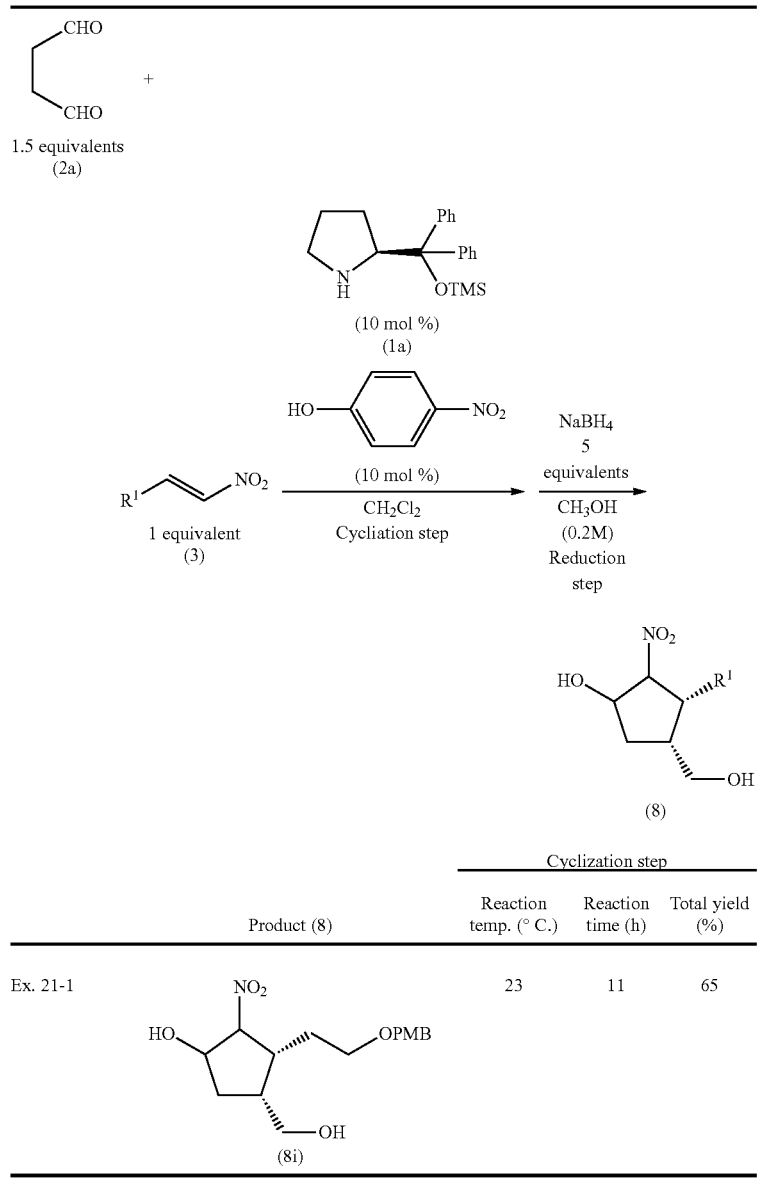

| | Product (8) | Cyclization step | | |
|---|---|---|---|---|
| | | Reaction temp. (° C.) | Reaction time (h) | Total yield (%) |
| Ex. 21-1 | (8i) | 23 | 11 | 65 |

*Instead of HO—⌬—NO₂, $C_6H_5CO_2H$ was used; the concentration was 0.33M in the reduction step
**Instead of HO—⌬—NO₂, $ClCH_2CO_2H$ was used
***Succinaldehyde (2a) (2.5 equivalents) was used The results of physical and chemical analyses of the mixture of four diastereomers of the diol product (8b)

$^1$H NMR (CDCl$_3$) δ 1.98-2.14 (1.6H, m), 2.24 (1.4H, dt, J=8.0, 14.0 Hz), 2.34-2.62 (1H, m), 3.42-3.59 (0.4H, m), 3.59-3.77 (1.6H, m), 3.21-3.39 (0.65H, m), 3.94-4.02 (0.35H, m), 4.46-4.53 (0.08H, m), 4.76 (0.1H, t, J=7.2 Hz), 4.63-4.78 (0.36H, m), 4.78-4.95 (0.46H, m), 6.88 (0.3H, d, J=9.2 Hz), 7.09 (0.3H, d, J=9.2 Hz), 7.14 (0.7H, dd, J=3.0, 8.4 Hz), 7.46 (0.7H, dd, J=3.0, 8.4 Hz);

TLC: Rf=0.22 (46%), 0.28 (36%), 0.39 (10%), 0.50 (8%) (developing solvent:ethyl acetate:hexane=2:1) (the ratio of diastereomers was determined based on the integrated ratio from $^1$H NMR)

The results of physical and chemical analyses of the mixture of four diastereomers of the diol product (8c)

$^1$H NMR (CDCl$_3$) δ 1.33-1.53 (1.1H, m), 1.53-1.79 (1.9H, m), 2.08-2.29 (0.61H, m), 2.30-2.57 (0.39H, m), 3.35-3.73 (3H, m), 3.78 (3H, s), 4.68 (0.48H, dd, J=10.2, 12.4 Hz), 4.72-4.81 (0.1H, m), 4.86 (0.42H, dd, J=5.2, 12.4 Hz), 6.85 (1.6H, dd, J=2.8, 9.6 Hz), 7.11 (1.6H, dd, J=2.8, 9.6 Hz), 7.19 (0.4H, d, J=5.6 Hz), 7.40 (0.4H, d, J=5.6 Hz);

TLC: Rf=0.21 (48%), 0.27 (42%), 0.35 (5%), 0.48 (5%) (developing solvent:ethyl acetate:hexane=2:1) (the ratio of diastereomers was determined based on the integrated ratio from $^1$H NMR)

The results of physical and chemical analyses of the mixture of four diastereomers of the diol product (8d)

$^1$H NMR (CDCl$_3$) δ 1.96 (0.85H, dd, J=1.6, 11.2 Hz), 2.09 (1.15H, ddd, J=5.6, 9.2, 14.4 Hz), 2.27 (1H, dd, J=8.0, 16.0 Hz), 2.44-2.57 (0.55H, m), 2.58-2.71 (0.45H, m), 3.61-3.76 (2H, m), 3.53 (0.56H, dd, J=5.6, 10.8 Hz), 4.16 (0.44H, dd, J=7.6, 10.8 Hz), 4.70 (0.25H, t, J=4.4 Hz), 4.79 (0.29H, dt, J=5.6, 8.0 Hz), 4.97 (0.23H, dd, J=5.6, 10.0 Hz), 5.03 (0.23H, dd, J=4.4, 10.8 Hz), 7.15-7.50 (4.6H, m), 7.62-7.90 (2.4H, m);

TLC: Rf=0.19 (29%), 0.25 (25%), 0.34 (23%), 0.44 (23%) (developing solvent:ethyl acetate:hexane=2:1) (the ratio of diastereomers was determined based on the integrated ratio from $^1$H NMR)

The results of physical and chemical analyses of the mixture of four diastereomers of the diol product (8e)

$^1$H NMR (CDCl$_3$) δ 1.78-1.94 (2H, m), 1.96-2.08 (1H, m), 2.21 (1H, dd, J=7.6, 14.0 Hz), 2.40-2.48 (0.26H, m), 2.52-2.69 (0.74H, m), 3.67-3.80 (2H, m), 3.62 (1H, dd, J=5.2, 10.8 Hz), 4.64 (0.18H, m), 4.73 (0.35H, dd, J=6.4, 14.0 Hz), 4.93 (0.31H, dd, J=6.4, 10.0 Hz), 5.00 (0.16H, dd, J=4.4, 10.4 Hz), 6.18 (1H, s), 6.30 (1H, bs), 7.34 (1H, d, J=6.4 Hz);

TLC: Rf=0.13 (35%), 0.22 (31%), 0.39 (18%), 0.47 (16%) (developing solvent:ethyl acetate:hexane=1:1) (the ratio of diastereomers was determined based on the integrated ratio from $^1$H NMR)

The results of physical and chemical analyses of the mixture of four diastereomers of the diol product (8f)

$^1$H NMR (CDCl$_3$) δ 1.58-1.71 (2H, m), 1.71-1.85 (1.16H, m), 1.86-1.98 (0.84H, m), 2.00-2.15 (0.71H, m), 2.18-2.28 (0.29H, m), 2.34-2.47 (0.84H, m), 2.55-2.72 (1.86H, m), 2.90 (0.3H, dt, J=9.2, 16.0 Hz), 3.10-3.20 (0.13H, m), 3.56 (0.24H, dd, J=6.4, 10.8 Hz), 3.59-3.71 (2.4H, m), 3.75 (0.36H, dd, J=5.6, 10.4 Hz), 4.40 (0.24H, dd, J=1.2, 5.6 Hz), 4.45-4.57 (0.57H, m), 4.64 (0.15H, dd, J=6.8, 13.2 Hz), 7.10-7.22 (2.9H, m), 7.27-7.33 (2.1H, m);

TLC: Rf=0.21 (32%), 0.29 (27%), 0.39 (25%), 0.48 (16%) (developing solvent: ethyl acetate:hexane=2:1) (the ratio of diastereomers was determined based on the integrated ratio from $^1$H NMR)

The results of physical and chemical analyses of the mixture of four diastereomers of the diol product (8g)

$^1$H NMR (CDCl$_3$) δ 1.48 (9H, s), 1.90-2.10 (1.04H, m), 2.28 (0.96H, dt, J=6.4, 14.8 Hz), 2.41-2.62 (1H, m), 3.33 (0.45H, dd, J=8.8 Hz), 3.62-3.81 (1.89H, m), 3.86 (0.66H, dd, J=3.2, 10.0 Hz), 3.37-3.48 (0.5H, m), 3.94-4.02 (0.5H, m), 4.55-4.68 (0.5H, m), 4.98 (0.17H, dd, J=6.4, 9.2 Hz), 5.05 (0.33H, dd, J=4.4, 11.2 Hz);

TLC: Rf=0.24 (31%), 0.31 (31%), 0.42 (19%), 0.52 (19%) (developing solvent: ethyl acetate:hexane=2:1) (the ratio of diastereomers was determined based on the integrated ratio from $^1$H NMR)

The results of physical and chemical analyses of the mixture of four diastereomers of the diol product (8h) supported the chemical structure thereof.

The results of physical and chemical analyses of the mixture of four diastereomers of the diol product (8i)

$^1$H NMR (CDCl$_3$) δ 1.50-1.86 (2H, m), 1.87-1.93 (1.4H, m), 1.99 (0.6H, dt, J=6.8, 13.6 Hz), 2.09-2.28 (1H, m), 2.54 (0.6H, dt, J=6.8, 13.6 Hz), 2.68-2.78 (0.13H, m), 2.89-3.00 (0.14H, m), 3.10-3.20 (0.13H, m), 3.45-3.58 (2.2H, m), 3.60 (1.4H, dd, J=1.2, 5.6 Hz), 3.60-3.72 (0.4H, m), 3.80 (3H, s), 4.31-4.51 (1.38H, m), 4.51-4.66 (0.62H, m), 6.85 (2H, dd, J=3.2, 8.8 Hz), 7.23 (2H, dd, J=3.2, 8.8 Hz);

TLC: Rf=0.26, 0.35, 0.53, 0.64 (developing solvent: ethyl acetate:hexane=2:1) (the ratio of diastereomers was determined based on the integrated ratio from $^1$H NMR)

Example 13-2 to Example 21-2

By the similar manner as in Example 1-2 (Dehydration step) except that the reaction conditions used were as shown in Table 6, desired nitrocyclopentene compounds which are dehydrated substances (9a to 9i) were obtained respectively as single diastereomer products. The results are summarized in Table 6. The results of physical and chemical analyses of the products by $^1$H NMR, $^{13}$C NMR, IR, HRMS (ESI), optical rotation measurement, optical purity measurement using a chiral column and Rf measurement by TLC are shown hereinbelow. The results of physical and chemical analyses of (9a) were the same as those obtained before and the results for (9b to 9i) support the chemical structures of the single isomers.

TABLE 6

| | Product (9) | Yield (%) | Optical yield (% ee) |
|---|---|---|---|
| Ex. 13-2 | (9a) | 75 | 95 |
| Ex. 14-2 | (9b) | 76 | 93 |
| Ex. 15-2 | (9c) | 70 | 91 |
| Ex. 16-2 | (9d) | 80 | 95 |
| Ex. 17-2 | (9e) | 58 | 85 |

TABLE 6-continued

[Reaction scheme: hydroxyl-nitrocyclopentane with R1 and CH2OH → Ac2O, pyridine → nitro-cyclopentene with R1 and CH2OAc (9)]

| Product (9) | Yield (%) | Optical yield (% ee) |
|---|---|---|
| Ex. 18-2  (9f) nitrocyclopentene with CH2CH2Ph and OAc | 70 | 94 |
| Ex. 19-2  (9g) nitrocyclopentene with CO2^tBu and OAc | 65 | 99 |
| Ex. 20-2  (9h) nitrocyclopentene with cyclohexyl and OAc | 60 | 97 |
| Ex. 21-2  (9i) nitrocyclopentene with CH2CH2OPMB and OAc | 71 | 92 |

The results of physical and chemical analyses of the dehydrated product (single isomer of ((1R,2S)-2-(4-bromophenyl)-3-nitrocyclopent-3-en-1-yl)methyl acetate) (9b)

$^1$H NMR (CDCl$_3$) δ 2.04 (3H, s), 2.43 (1H, ddt, J=2.8, 4.8, 19.2 Hz), 2.67 (1H, m), 2.90 (1H, ddt, J=2.8, 8.8, 16.4 Hz), 3.79 (1H, dt, J=7.2, 11.2 Hz), 4.09 (1H, dd, J=6.8, 11.2 Hz), 4.12-4.16 (1H, m), 4.17 (1H, dd, J=6.0, 11.2 Hz), 7.05 (2H, dd, J=2.4, 9.2 Hz), 7.14 (1H, dd, J=2.8, 4.4 Hz), 7.44 (2H, dd, J=2.4, 9.2 Hz);

$^{13}$C NMR (CDCl$_3$) δ 20.7, 32.4, 46.4, 51.0, 65.6, 121.3, 128.5 (2C), 132.1 (2C), 138.0, 139.8, 153.3, 170.8;

IR (neat) ν 1739, 1550, 1514, 1488, 1240, 1038, 1010 cm$^{-1}$;

HRMS (ESI): [M+Na]$^+$ calculated for C$_{14}$H$_{14}$NO$_4$BrNa: 362.0004. found: 362.0011;

[α]$_D^{20}$+48.2 (c 0.71, CHCl$_3$)

Optical yield: 93% ee (optical yield was such that when analyzed by high performance liquid column chromatography using a Chiralpak IB column (Daicel Corporation) with an elution solvent (hexane:isopropanol=80:1) at an elution speed of 1.0 mL/min, the major enantiomer had t$_R$=24.9 min and the minor enantiomer had t$_R$=28.0 min);

TLC: Rf=0.31 (developing solvent:ethyl acetate:hexane=1:3)

The results of physical and chemical analyses of the dehydrated product (single isomer of ((1R,2S)-2-(4-methoxyphenyl)-3-nitrocyclopent-3-en-1-yl)methyl acetate) (9c)

$^1$H NMR (CDCl$_3$) δ 2.05 (3H, s), 2.41 (1H, dt, J=4.8, 19.6 Hz), 2.69 (1H, m), 2.90 (1H, ddt, J=2.8, 8.8, 16.4 Hz), 3.77 (1H, s), 4.10 (1H, dd, J=6.4, 11.2 Hz), 4.12-4.15 (1H, m), 4.17 (1H, dd, J=6.4, 11.2 Hz), 6.85 (2H, dd, J=2.8, 9.6 Hz), 7.09 (2H, dd, J=2.8, 9.6 Hz), 7.11 (1H, s);

$^{13}$C NMR (CDCl$_3$) δ 20.8, 32.4, 46.5, 50.6, 55.2, 65.8, 114.3 (2C), 127.9 (2C), 132.7, 137.3, 153.9, 158.8, 170.8;

IR (neat) ν 1740, 1511, 1361, 1240, 1179, 1034 cm$^{-1}$;

HRMS (ESI): [M+Na]$^+$ calculated for C$_{7.5}$H$_{17}$NO$_5$Na: 314.1004. found: 314.0990;

[α]$_D^{20}$+85.8 (c 0.67, CHCl$_3$);

Optical yield: 91% ee (optical yield was such that when analyzed by high performance liquid column chromatography using a Chiralpak IB column (Daicel Corporation) with an elution solvent (hexane:isopropanol=80:1) at an elution speed of 1.0 mL/min, the major enantiomer had t$_R$=25.5 min and the minor enantiomer had t$_R$=28.4 min);

TLC: Rf=0.29 (developing solvent:ethyl acetate:hexane=1:3)

The results of physical and chemical analyses of the dehydrated product (single isomer of ((1R,2S)-2-(naphthalen-2-yl)-3-nitrocyclopent-3-en-1-yl) methyl acetate) (9d)

$^1$H NMR (CDCl$_3$) δ 20.7 (3H, s), 2.48 (1H, bd, J=19.2 Hz), 2.74-2.88 (1H, m), 2.98 (1H, ddt, J=2.8, 8.8, 19.2 Hz), 4.16 (1H, dd, J=6.8, 11.2 Hz), 4.22 (1H, dd, J=6.8, 11.2 Hz), 4.36 (1H, bs), 7.21 (1H, s), 7.30 (1H, dd, J=1.6, 8.4 Hz), 7.41-7.54 (2H, m), 7.54 (1H, s), 7.74-7.89 (3H, m);

$^{13}$C NMR (CDCl$_3$) δ 20.8, 32.6, 46.4, 51.5, 65.8, 124.8, 125.6, 125.9, 126.4, 127.7 (2C), 129.0, 132.7, 133.5, 138.0 (2C), 153.6, 170.9;

IR (neat) ν 1740, 1513, 1359, 1237, 1038, 817.6 cm$^{-1}$;

HRMS (ESI): [M+Na]$^+$ calculated for C$_{18}$H$_{17}$NO$_4$Na: 334.1055. found: 334.1049;

[α]$_D^{18}$+889 (c 0.24, CHCl$_3$);

Optical yield: 95% ee (optical yield was such that when analyzed by high performance liquid column chromatography using a Chiralpak IB column (Daicel Corporation) with an elution solvent (hexane:isopropanol=80:1) at an elution speed of 1.0 mL/min, the major enantiomer had t$_R$=25.9 min and the minor enantiomer had t$_R$=31.9 min);

TLC: Rf=0.31 (developing solvent:ethyl acetate:hexane=1:3)

The results of physical and chemical analyses of the dehydrated product (single isomer of ((1R,2R)-2-(furan-2-yl)-3-nitrocyclopent-3-en-1-yl)methyl acetate) (9e)

$^1$H NMR (CDCl$_3$) δ 20.5 (3H, s), 2.41 (1H, dd, J=4.4, 14.8 Hz), 2.89 (1H, d, J=2.0 Hz), 2.80-2.99 (1H, m), 4.08 (1H, dd, J=4.4, 6.4 Hz), 4.14 (1H, dd, J=4.4, 6.4 Hz), 4.28 (1H, s), 6.14 (1H, s) 6.28 (1H, s), 7.09 (1H, s), 7.29 (1H, s);

$^{13}$C NMR (CDCl$_3$) δ 20.8, 32.3, 43.2, 44.6, 65.5, 106.5, 110.5, 138.2, 142.0, 151.4, 152.3, 170.9;

IR (neat) ν 1740, 1515, 1361, 1234, 1037, 1011, 737.6 cm$^{-1}$;

HRMS (ESI): [M+Na]$^+$ calculated for C$_{12}$H$_{13}$NO$_5$Na: 274.0691. found: 274.0697;

[α]$_D^{21}$+43.6 (c 0.46, CHCl$_3$);

Optical yield: 92% ee (optical yield was such that when analyzed by high performance liquid column chromatography using a Chiralpak IB column (Daicel Corporation) with an elution solvent (hexane:isopropanol=80:1) at an elution speed of 1.0 mL/min, the major enantiomer had t$_R$=18.2 min and the minor enantiomer had t$_R$=18.4 min);

TLC: Rf=0.44 (developing solvent:ethyl acetate:hexane=1:3)

The results of physical and chemical analyses of the dehydrated product (single isomer of ((1R,2R)-3-nitro-2-phenethylcyclopent-3-en-1-yl)methyl acetate) (9f)

$^1$H NMR (CDCl$_3$) δ 1.72-1.85 (1H, m), 2.04 (3H, s), 2.05-2.18 (2H, m) 2.31 (1H, dd, J=2.4, 19.6 Hz), 2.57-2.74 (2H, m), 2.81 (1H, ddt, J=2.8, 8.4, 19.6 Hz), 3.03 (1H, dd, J=2.4, 6.0 Hz), 3.98 (2H, dd, J=1.6, 7.2 Hz), 6.94 (1H, bs), 7.13-7.21 (3H, m), 7.26 (2H, d, J=7.6 Hz);

$^{13}$C NMR (CDCl$_3$) δ 20.8, 20.9, 32.3, 32.8, 33.4, 41.0, 44.9, 66.6, 126.1, 128.3 (2C), 128.5 (2C), 136.8, 141.0, 154.4, 171.0;

IR (neat) ν 1741, 1510, 1356, 1236, 1036, 701.0, 439.6 cm$^{-1}$;

HRMS (ESI): [M+Na]$^+$ calculated for C$_{16}$H$_{19}$NO$_4$Na: 312.1212. found: 312.1225;

[α]$_D^{20}$+7.9 (c 0.95, CHCl$_3$);

Optical yield: 94% ee (optical yield was such that when analyzed by high performance liquid column chromatography using a Chiralpak IB column (Daicel Corporation) with an elution solvent (hexane:isopropanol=30:1) at an elution speed of 1.0 mL/min, the major enantiomer had t$_R$=30.7 min and the minor enantiomer had t$_R$=43.5 min);

TLC: Rf=0.41 (developing solvent:ethyl acetate:hexane=1:3)

The results of physical and chemical analyses of the dehydrated product (single isomer of ((1R,5R)-tert-butyl 5-(acetoxymethyl)-2-nitrocyclopent-2-enecarboxylate) (9g)

$^1$H NMR (CDCl$_3$) δ 1.45 (9H, s), 2.07 (3H, s), 2.40 (1H, bd, J=18.4 Hz), 2.80-2.98 (2H, m), 3.75 (1H, bs), 4.13 (2H, dd, J=5.6, 10.8 Hz), 7.05 (1H, s);

$^{13}$C NMR (CDCl$_3$) δ 20.8, 27.8 (3C), 33.0, 41.4, 51.8, 65.6, 82.2, 138.8, 150.3, 170.1, 170.8;

IR (neat) ν 1741, 1559, 1521, 1368, 1238, 1154, 1040 cm$^{-1}$;

HRMS (ESI): [M+Na]$^+$ calculated for C$_{13}$H$_{19}$NO$_6$Na: 308.1110. found: 308.1108;

[α]$_D^{20}$−15.8 (c 0.30, CHCl$_3$);

Optical yield: 99% ee (optical yield was such that when analyzed by high performance liquid column chromatography using a Chiralpak IB column (Daicel Corporation) with an elution solvent (hexane:isopropanol=80:1) at an elution speed of 1.0 mL/min, the major enantiomer had t$_R$=13.3 min and the minor enantiomer had t$_R$=15.3 min);

TLC: Rf=0.34 (developing solvent:ethyl acetate:hexane=1:3)

The results of physical and chemical analyses of the dehydrated product (9h) supported the chemical structure thereof.

The results of physical and chemical analyses of the dehydrated product (single isomer of ((1R,2R)-2-(2-(4-methoxybenzolyoxy)ethyl)-3-nitrocyclopent-3-en-1-yl)methyl acetate) (9i)

$^1$H NMR (CDCl$_3$) δ 1.76-1.89 (1H, m), 2.03 (3H, s), 2.04-2.10 (1H, m), 2.27 (1H, dd, J=2.4, 18.8 Hz), 2.59-2.68 (1H, m), 2.73 (1H, ddt, J=2.8, 8.4, 19.2 Hz), 3.10 (1H, m), 3.51 (2H, t, J=6.0 Hz), 3.79 (3H, s), 3.98 (2H, d, J=6.8 Hz), 4.38 (2H, s), 6.86 (2H, dd, J=3.2, 8.8 Hz) 6.90 (1H, s), 7.23 (2H, dd, J=3.2, 8.8 Hz);

$^{13}$C NMR (CDCl$_3$) δ 19.2, 30.1, 30.7, 39.7, 42.6, 53.7, 65.8, 66.1, 71.1, 126.1, 128.3 (2C), 128.5 (2C), 136.8, 141.0, 154.4, 171.0;

IR (neat) ν 1740, 1613, 1513, 1360, 1246, 1094, 1034 cm$^{-1}$;

HRMS (ESI): [M+Na]$^+$ calculated for C$_{18}$H$_{23}$NO$_6$Na: 372.1423. found: 372.1433;

[α]$_D^{20}$−10.7 (c 0.26, CHCl$_3$);

Optical yield: 92% ee (optical yield was such that when analyzed by high performance liquid column chromatography using a Chiralpak IB column (Daicel Corporation) with an elution solvent (hexane:isopropanol=80:1) at an elution speed of 1.0 mL/min, the major enantiomer had t$_R$=29.7 min and the minor enantiomer had t$_R$=33.9 min);

TLC: Rf=0.27 (developing solvent:ethyl acetate:hexane=1:3)

The compounds obtained in Examples 1 to 21 are useful intermediates to derive PGEs and PGFs.

Example 22 Cyclization Step and Homologation Step

As shown in the following chemical reaction formula (XI), the cyclization step and then the homologation step of the obtained intermediate without purification were carried out.

(XI)

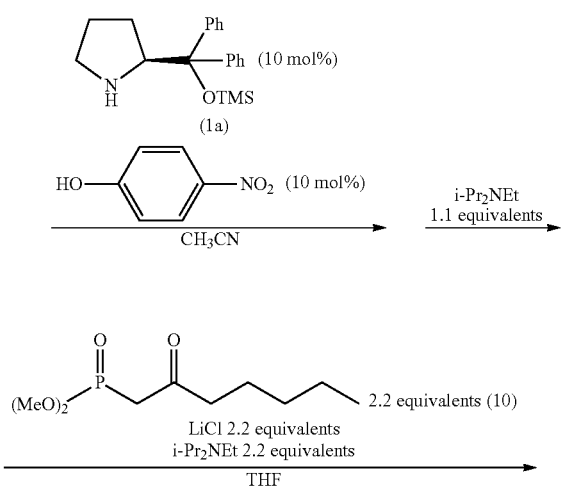

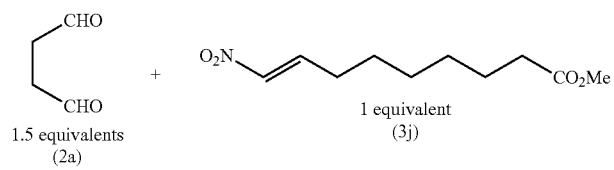

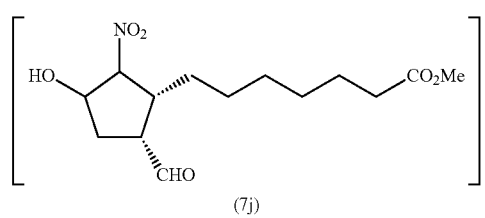

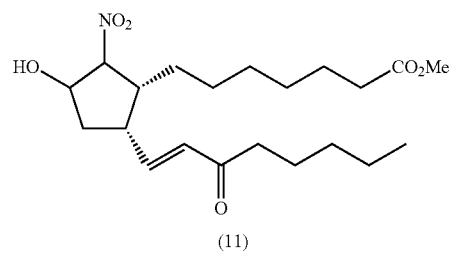

(11)

First, under an argon atmosphere, to a solution of methyl 9-nitro-8-nonenoate (3j) (1.72 g, 8 mmol) as the E-α,β-unsaturated nitroalkene compound and succinaldehyde (2a) (1.03 g, 12 mmol) as the 1,4-butanedione compound in acetonitrile (8 mL) which corresponded to the non-oxygen atom-containing water-soluble organic solvent were added (S)-2-(diphenyl((trimethylsilyl)oxy)methyl)pyrrolidine (1a) (260.4 mg, 0.8 mmol) as the proline derivative and p-nitrophenol (111.4 mg, 0.8 mmol) as the acid at a room temperature and the mixture was stirred at the same temperature for 16 hours. The main products were visualized as a diastereomer mixture by TLC with the spots of the aldehyde reaction products (7j) at the Rf values=0.32 to 0.43 (developing solvent:ethyl acetate:hexane=1:1). After confirming the elimination of the spot of the α,β-unsaturated nitroalkene compound (3j) by TLC, the reaction solution was cooled to 0° C., added with diisopropylethylamine (1.5 ml, 8.8 mmol) and stirred at 0° C. for 30 minutes to obtain the aldehyde (7j)-containing reaction solution without purification.

Meanwhile, under an argon atmosphere, to a solution of a phosphonate, i.e. dimethyl (2-oxoheptyl)phosphonate (10) (3.92 g, 17.6 mmol) in THF (20 mL) was added lithium chloride (746 mg, 17.6 mmol) at a room temperature and the solution was stirred at the same temperature until complete dissolution of lithium chloride. After confirming that lithium chloride was dissolved completely, diisopropylethylamine (3 ml, 17.6 mmol) was added at a room temperature and the solution was stirred at the same temperature for 1 hour to prepare a Horner-Wadsworth-Emmons reagent (HWE reagent) which was used without purification.

To the aldehyde (7j)-containing reaction solution was then added the prepared HWE reagent at 0° C., and the mixture was brought to a room temperature and stirred for 4 hours. A saturated ammonium chloride aqueous solution was added to terminate the reaction and the organic matter was extracted with ethyl acetate 3 times. The combined organic layer was washed with a saturated aqueous sodium chloride solution and dried with magnesium sulfate. Low-boiling organic compounds such as solvents were distilled off under reduced pressure prior to purification by silica gel column chromatography (elution solvent:ethyl acetate:hexane=1:5→1:3) to obtain a desired enone (11) (2.55 g, 6.4 mmol) as a mixture of four diastereomers (Rf values by TLC=0.29, 0.35 (developing solvent:ethyl acetate:hexane=1:2)) with the yield of 80%.

The results of physical and chemical analyses of the diastereomer mixture by $^1$H NMR, $^{13}$C NMR, IR, HRMS (ESI) and Rf measurement by TLC are shown hereinbelow. The results of physical and chemical analyses support the chemical structure of the enone (11).

The results of physical and chemical analyses of the mixture of four diastereomers of the enone (methyl 7-((1R,5S)-3-hydroxy-2-nitro-5-((E)-3-oxooct-1-enyl)cyclopentyl)heptanoate) (11)

$^1$H NMR (CDCl$_3$) δ 0.86 (3H, t, J=7.6 Hz), 1.20-1.35 (10H, m), 1.48-1.64 (6H, m), 1.92-2.02 (1H, m), 2.02-2.10 (1H, m), 2.25 (2H, t, J=7.6 Hz), 2.31-2.42 (1H, m), 2.51 (2H, t, J=7.6 Hz), 2.66-2.78 (1H, m), 3.62 (3H, s), 4.51 (1H, dd, J=3.6, 7.6 Hz), 4.59-4.66 (1H, m), 6.11 (1H, d, J=16.0 Hz), 6.56-6.64 (0.16H, m), 6.67 (0.6H, dd, J=8.8, 16.0 Hz), 6.72-6.84 (0.24H, m)

$^{13}$C NMR (CDCl$_3$) δ 13.8, 22.4, 23.8, 24.7, 26.8, 28.7, 29.1, 31.4, 32.5, 33.9, 39.4, 40.6, 45.2, 49.4, 51.4, 76.1, 97.6, 130.7, 147.5, 174.2, 200.5;

IR (neat) ν 3455, 2931, 2861, 1735, 1666, 1627, 1627, 1550, 1442, 1373, 1249, 1172, 1110, 1064, 987.3, 763.6 cm$^{-1}$;

HRMS (ESI): [M+Na]$^+$ calculated for C$_{21}$H$_{35}$NO$_6$Na: 420.2362. found: 420.2355

TLC: Rf=0.29, 0.35 (developing solvent:ethyl acetate:hexane=1:2)

Example 23 Enone Asymmetrical Reduction Step and Dehydration Step

As shown in the following chemical reaction formula (X), the mixture of four diastereomers obtained in Example 22 was subjected to the enone asymmetrical reduction step and the obtained reduced substance without purification was subjected to the dehydration step.

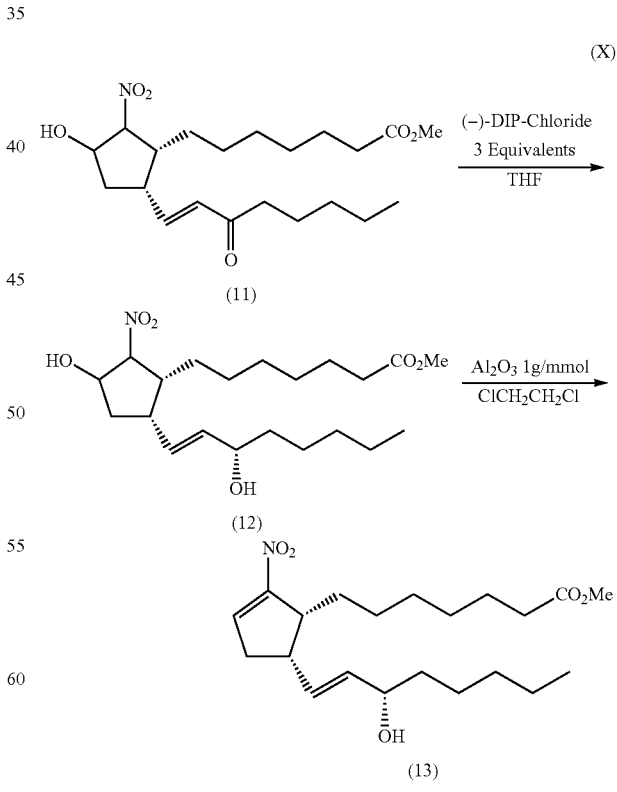

(X)

First, under an argon atmosphere, to a solution of the enone (11) as the mixture of four diastereomers (60 mg, 0.150 mmol) in THF (395 μL) was added (−)-DIP-Chloride ((−)-B-chlorodiisopinocampheylborane; 1.7 M solution in THF, 266 μL, 0.45 mmol) at −20° C. and the mixture was stirred at the same temperature for 8 hours. The main products were visualized by TLC at Rf=0.26, 0.30 (developing solvent:hexane:ethyl acetate=1:1). After confirming the elimination of the enone (11) by TLC, methanol was added prior to raising the temperature to 0° C. The solution was then added with water, stirred at the same temperature for 30 minutes and added with 1 N HCl prior to the extraction of the organic matter with ethyl acetate for 3 times. The combined organic layer was washed with a saturated aqueous sodium chloride solution and dried with magnesium sulfate. Low-boiling organic compounds such as solvents were distilled off under reduced pressure prior to purification by silica gel column chromatography (elution solvent:ethyl acetate:hexane=1:10→1:1) to obtain a desired allylalcohol (12) (42.6 mg, 0.107 mmol) as a mixture of four diastereomers (Rf by TLC=0.26, 0.30 (ethyl acetate:hexane=1:1)) with the yield of 71%. The diastereo ratio at this time, although it was determined after the following dehydration reaction, was 93.5:6.5.

The results of physical and chemical analyses of the diastereomer mixture by $^1$H NMR, $^{13}$C NMR, IR, HRMS (ESI) and Rf measurement by TLC are shown hereinbelow. The results of physical and chemical analyses support the chemical structure of the allylalcohol (12).

The results of physical and chemical analyses of the mixture of four diastereomers of the allylalcohol (methyl 7-((1R,5S)-3-hydroxy-5-((S,E)-3-hydroxyoct-1-enyl)-2-nitrocyclopentyl)heptanoate)

$^1$H NMR (CDCl$_3$) δ 0.88 (3H, t, J=6.8 Hz), 1.20-1.35 (12H, m), 1.41-1.52 (4H, m), 1.52-1.63 (4H, m), 1.86-1.95 (1H, m), 1.95-2.04 (1H, m), 2.21-2.31 (1H, m), 2.28 (2H, t, J=7.2 Hz), 2.48-2.60 (1H, m), 3.65 (3H, s), 4.03-4.11 (1H, m), 4.48 (1H, dd, J=3.6, 8.0 Hz), 4.58-4.66 (1H, m), 5.45-5.62 (2H, m)

$^{13}$C NMR (CDCl$_3$) δ 13.9, 22.5, 24.6, 25.0, 26.3, 28.7, 29.0, 31.7, 32.1, 33.9, 37.3, 39.9, 45.0, 49.6, 51.4, 72.4, 76.2, 97.9, 132.0, 134.8, 174.3;

IR (neat) ν 3440, 2931, 2861, 2360, 1735, 1550, 1442, 1373, 1257, 1172, 1110, 1056, 971.9, 863.9, 763.6 cm$^{-1}$;

HRMS (ESI): [M+Na]$^+$ calculated for C$_{21}$H$_{37}$NO$_6$Na: 422.2519. found: 422.2511

Rf=0.26, 0.30 (developing solvent:ethyl acetate:hexane=1:1)

Next, under an argon atmosphere, to a solution of the obtained allylalcohol (12) (339 mg, 0.845 mmol) in 1,2-dichloroethane (1.7 ml) was added acidic activated alumina (Sigma-Aldrich, Catalogue No. 199966, 282 mg) prior to raising the temperature to 60° C. and stirring at the same temperature. After 12 and 24 hours, 282 mg of acidic activated alumina was added, respectively. The main products were visualized by TLC at Rf=0.62 (developing solvent:hexane:ethyl acetate=1:1). After 48 hours and confirming the elimination of the allylalcohol (12) by TLC, acidic activated alumina was removed by filtration through Celite. Low-boiling organic compounds such as solvents were distilled off under reduced pressure to obtain a desired nitroalkene (13) as a diastereomer mixture (290 mg, 0.76 mmol) with the yield of 90%. At this time, the configuration between the side chains corresponding to the α chain and the ω chain from the cyclopentane ring was cis:trans=6.7:1.

The results of physical and chemical analyses of the main components obtained by purification of the mixture by $^1$H NMR, $^{13}$C NMR, IR, HRMS (ESI), optical purity and Rf measurement by TLC are shown hereinbelow. The results of physical and chemical analyses support the chemical structure of the nitroalkene (13). The results of physical and chemical analyses of the nitroalkene (methyl 7-((1R,5S)-5-((S,E)-3-hydroxyoct-1-enyl)-2-nitrocyclopent-2-en yl)heptanoate)

$^1$H NMR (CDCl$_3$) δ 0.89 (3H, t, J=6.8 Hz), 1.20-1.40 (10H, m), 1.42-1.66 (8H, m), 1.67-1.79 (1H, m), 2.26-2.38 (1H, m), 2.29 (2H, t, J=7.6 Hz), 2.75-2.88 (2H, m), 2.96 (1H, bs), 3.66 (3H, s), 4.01-4.10 (1H, m), 5.51 (1H, dd, J=6.8, 15.6 Hz), 5.67 (1H, dd, J=6.8, 15.6 Hz), 6.91 (1H, s);

$^{13}$C NMR (CDCl$_3$) δ 13.9, 22.5, 24.7, 25.0, 26.0, 28.9, 29.3, 31.3, 31.7, 33.9, 35.8, 37.5, 45.1, 48.4, 51.4, 72.5, 133.1, 133.4, 136.6, 154.7, 174.2;

IR (neat) ν 2930, 2857, 1739, 1636, 1550, 1512, 1465, 1456, 1436, 1354, 1256, 1200, 1172, 972.9, 782.9, 728.9 cm$^{-1}$;

HRMS (ESI): [M+Na]$^+$ calculated for C$_{21}$H$_{35}$NO$_5$Na: 404.2413. found: 404.2423;

Optical yield: 94% ee (optical yield was such that when analyzed by high performance liquid column chromatography using a Chiralpak IC column (Daicel Corporation) with an elution solvent (hexane:isopropanol=10:1) at an elution speed of 1.0 mL/min, the major enantiomer had t$_R$=19.3 min and the minor enantiomer had t$_R$=31.1 min; based on the area ratio, the enantiomeric excess was 94% ee);

Rf=0.62 (developing solvent:ethyl acetate:hexane=1:1)

The compounds obtained in Examples 22 and 23 are useful intermediates to derive PGEs and PGFs, particularly PGE$_1$ according to the method described above or well known methods. The compounds obtained in Examples 22 and 23 have the inversed configuration of the group corresponding to the ω side chain compared to the natural PGE$_1$. Alternatively to Example 22, a proline derivative having an inverted configuration may be optionally used in order to invert the configuration of the group corresponding to the α side chain as shown in the chemical reaction formula (IX).

INDUSTRIAL APPLICABILITY

The method for producing a five-membered ring-containing compound and the five-membered ring-containing compounds obtained thereby according to the present invention can be used as synthetic intermediates of various physiologically active substances typified by PGs such as PGEs and PGFs.

The invention claimed is:
1. A method for producing a five-membered ring-containing compound represented by the following chemical formula (II):

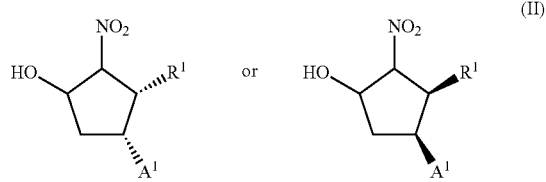

wherein in the formula (II), R$^1$ may contain a substituent and is selected from a hydrocarbon ring group, a heterocyclic group, a hydrocarbon ring-containing alkyl group, a heterocycle-containing alkyl group, an alkyl group, an alkenyl group, an alkynyl group, an alkyl thioether-containing alkyl group, a heterocyclic group-containing alkyl thioether group, a hydrocarbon ring group-containing alkyl ether group and an alkyloxycarbonyl group; A$^1$ is an aldehyde group or a hydroxymethyl group obtained by reduction thereof; and among the configuration symbols, represents the α-configuration and represents the β-configuration, the method comprising a cyclization step of condensing and cyclizing an α,β-unsaturated nitro compound represented by the following chemical formula (I):

(I)

wherein in the formula (I), $R^1$ is as described above,
with a 1,4-butanedione compound, in the presence of a catalyst formed by a compound having a pyrrolidine ring and an optically active α-carbon relative to the nitrogen on the ring, in a water-insoluble organic solvent and/or a non-oxygen atom-containing water-soluble organic solvent.

2. The method for producing a five-membered ring-containing compound according to claim 1, further comprising, after the cyclization step, a reduction step of reducing, with a reducing agent, the $A^1$ that is the aldehyde group to the hydroxymethyl group.

3. The method for producing a five-membered ring-containing compound according to claim 1, wherein the catalyst is a proline derivative represented by the following chemical formula (III):

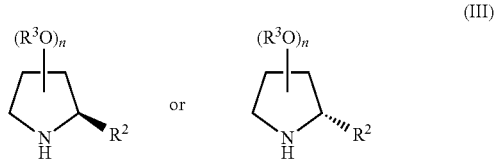
(III)

wherein in the formula (III), $R^2$ is a carboxyl group, a tetrazole group or a —$C(R^4)(R^5)OR^6$ group [wherein $R^4$ and $R^5$ respectively and independently may contain a substituent and are selected from a hydrocarbon aromatic ring group, a heteroaromatic ring group and an alkyl group; and $R^6$ is a hydrogen atom, a silyl group or an alkyl group]; $R^3$ represents a protective group; n represents a number of 0 to 1; and configuration symbols are the same as above.

4. The method for producing a five-membered ring-containing compound according to claim 3, wherein the proline derivative represented by the chemical formula (III) corresponds to:

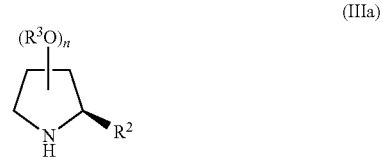
(IIIa)

wherein in the formula (IIIa), all symbols are the same as above,
and the five-membered ring-containing compound represented by the chemical formula (II) corresponds to:

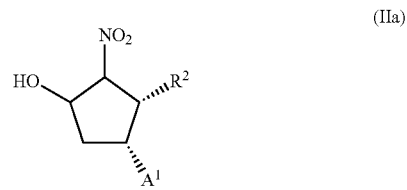
(IIa)

wherein in the formula (IIIa), all symbols are the same as above.

5. The method for producing a five-membered ring-containing compound according to claim 3, wherein the proline derivative represented by the chemical formula (III) corresponds to:

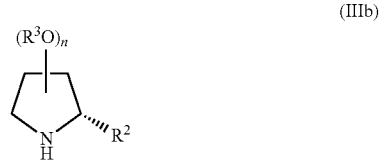
(IIIb)

wherein in the formula (IIIb), all symbols are the same as above,
and the five-membered ring-containing compound represented by the chemical formula (II) corresponds to:

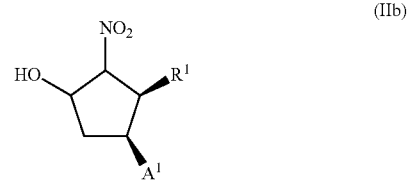
(IIb)

wherein in the formula (IIb), all symbols are the same as above.

6. The method for producing a five-membered ring-containing compound according to claim 1, wherein the water-insoluble organic solvent is at least one selected from a halogen-containing organic solvent, an aromatic organic solvent, a hydrocarbon organic solvent and an acyclic ether organic solvent, and the non-oxygen atom-containing water-soluble organic solvent is a nitrile-substituted hydrocarbon organic solvent.

7. The method for producing a five-membered ring-containing compound according to claim 6, wherein the water-insoluble organic solvent is the halogen-containing organic solvent selected from dichloromethane, dichloroethane and chloroform; the aromatic organic solvent selected from benzene, toluene and xylene; the hydrocarbon organic solvent selected from pentane, hexane and heptane; and/or the acyclic ether organic solvent that is diethyl ether, and the non-oxygen atom-containing water-soluble organic solvent is the nitrile-substituted hydrocarbon organic solvent that is acetonitrile.

8. The method for producing a five-membered ring-containing compound according to claim 1, wherein the cyclization step is performed in the presence of both the catalyst and an acid.

9. The method for producing a five-membered ring-containing compound according to claim 8, wherein the acid has a pKa in water at 25° C. of 4 to 10.

10. The method for producing a five-membered ring-containing compound according to claim 8, wherein the acid is at least one free acid selected from the group consisting of a fatty acid derivative containing 1 to 3 carbon atoms, an aromatic carboxylic acid derivative, a hydroxyaromatic derivative and a perfluoroalkyl group-containing alcohol.

11. The method for producing a five-membered ring-containing compound according to claim 1, wherein the substituent in $R^1$ of the chemical formula (I) is at least one selected from the group consisting of a linear or branched alkoxy group containing 1 to 4 carbon atoms, an ester group and a halogen atom.

12. The method for producing a five-membered ring-containing compound according to claim 1, wherein the catalyst is (S)-2-(diphenyl((trimethylsilyl)oxy)methyl)pyrrolidine or (R)-2-(diphenyl((trimethylsilyl)oxy)methyl)pyrrolidine.

13. The method for producing a five-membered ring-containing compound according to claim 2, wherein the reducing agent is at least one selected from the group consisting of $NaBH_4$, $NaBH_3CN$, $B_2H_6$, $BH_3 \cdot Me_2S$, $LiAlH_4$, $NaB(O_2CCH_3)_3H$ and $LiBH(C_2H_5)_3$.

14. A five-membered ring-containing compound represented by the following chemical formula (IV):

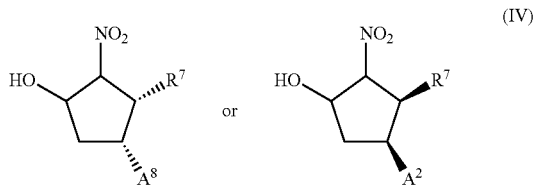

(IV)

wherein in the formula (IV), $R^7$ may contain a substituent and is selected from a hydrocarbon ring group, a heterocyclic group, a hydrocarbon ring-containing alkyl group, a heterocycle-containing alkyl group, an alkyl group, an alkenyl group, an alkynyl group, an alkyl thioether-containing alkyl group, a heterocyclic group-containing alkyl thioether group, a hydrocarbon ring group-containing alkyl ether group and an alkyloxycarbonyl group; $A^2$ is an aldehyde group or a hydroxymethyl group; and among the configuration symbols, ⫽⫽⫽ represents the α-configuration and ▲ represents the β-configuration.

15. The five-membered ring-containing compound according to claim 14, wherein in the chemical formula (IV), the $R^7$ may contain a substituent and is selected from a cyclohexyl group, a phenyl group, a naphthyl group, a furyl group, a phenethyl group, a benzyloxy ethyl group and an alkyloxycarbonyl group.

16. The five-membered ring-containing compound according to claim 14, wherein in the chemical formula (IV), the $R^7$ is any of those represented by the following chemical formula (V):

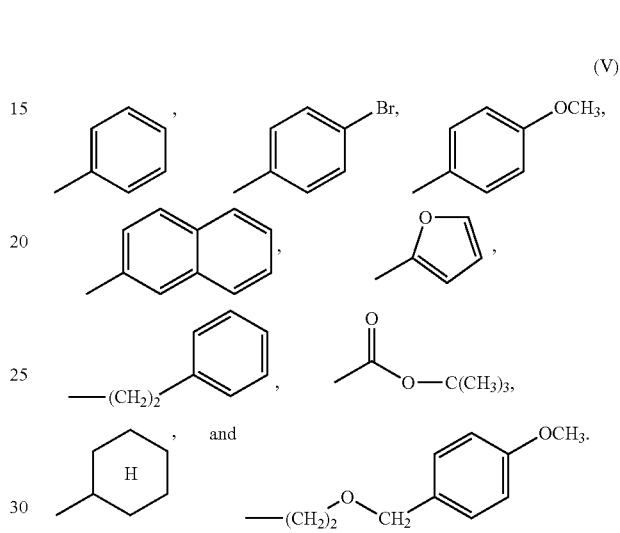

(V)

* * * * *